United States Patent [19]

Rhyne

[11] Patent Number: 4,881,549

[45] Date of Patent: Nov. 21, 1989

[54] APPARATUS AND METHOD FOR OBTAINING ULTRASONIC BACKCATTER MEASUREMENT FROM TISSUE

[75] Inventor: Theodore L. Rhyne, Whitefish Bay, Wis.

[73] Assignee: Marquette Electronics, Milwaukee, Wis.

[21] Appl. No.: 219,895

[22] Filed: Jul. 14, 1988

Related U.S. Application Data

[63] Continuation of Ser. No. 55,732, May 29, 1987, abandoned.

[51] Int. Cl.[4] .............................................. A61B 8/00
[52] U.S. Cl. ................................. 128/660.07; 73/602
[58] Field of Search ...................... 128/660.06, 660.07; 73/597, 599, 602

[56] References Cited

U.S. PATENT DOCUMENTS

| | | | |
|---|---|---|---|
| 4,043,181 | 8/1977 | Nigam | 128/610 |
| 4,197,524 | 4/1980 | Hassler | 128/660.06 X |
| 4,470,303 | 9/1984 | O'Donnell | 73/633 X |
| 4,509,524 | 4/1985 | Mioja | 128/660.06 |
| 4,562,540 | 12/1985 | Devaney | 73/602 X |
| 4,662,222 | 5/1987 | Johnson | 73/602 |
| 4,688,428 | 8/1987 | Nicolas | 73/602 |

OTHER PUBLICATIONS

Sheng, K. K. et al., "Scattering of Ultrasound by Blood", IEEE BME Trans., vol. BME—23, No. 6, pp. 460–467, Nov. 1976.

Primary Examiner—Francis Jaworski
Attorney, Agent, or Firm—Andrus, Sceales, Starke & Sawall

[57] ABSTRACT

Optimal measurement of ultrasonic random backscatter from the myocardium is obtained by band limiting and whitening the received signal, squaring, summing and scaling same. The whitening is carried out for all spectrally altering factors to which the ultrasonic signal has been subjected. This includes whitening for the power law frequency response characterstics of the myocardium itself. Scaling includes a factor accounting for the energy of the effective transmitted ultrasonic signal and a factor providing appropriate units of measurement. The optimal measurement may be time averaged over one or more heartbeats for use in the diagnosis of ischemia or other cardiac conditions. It may be subjected to discrete Fourier transform analysis, to obtain its amplitude modulation and phase characteristics for similar purposes.

60 Claims, 12 Drawing Sheets

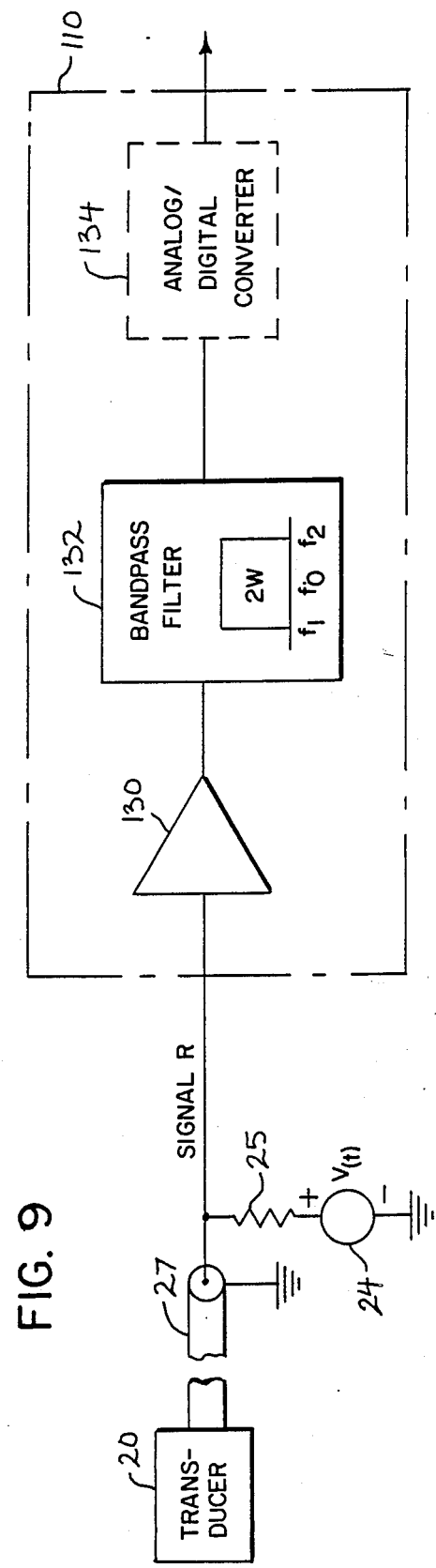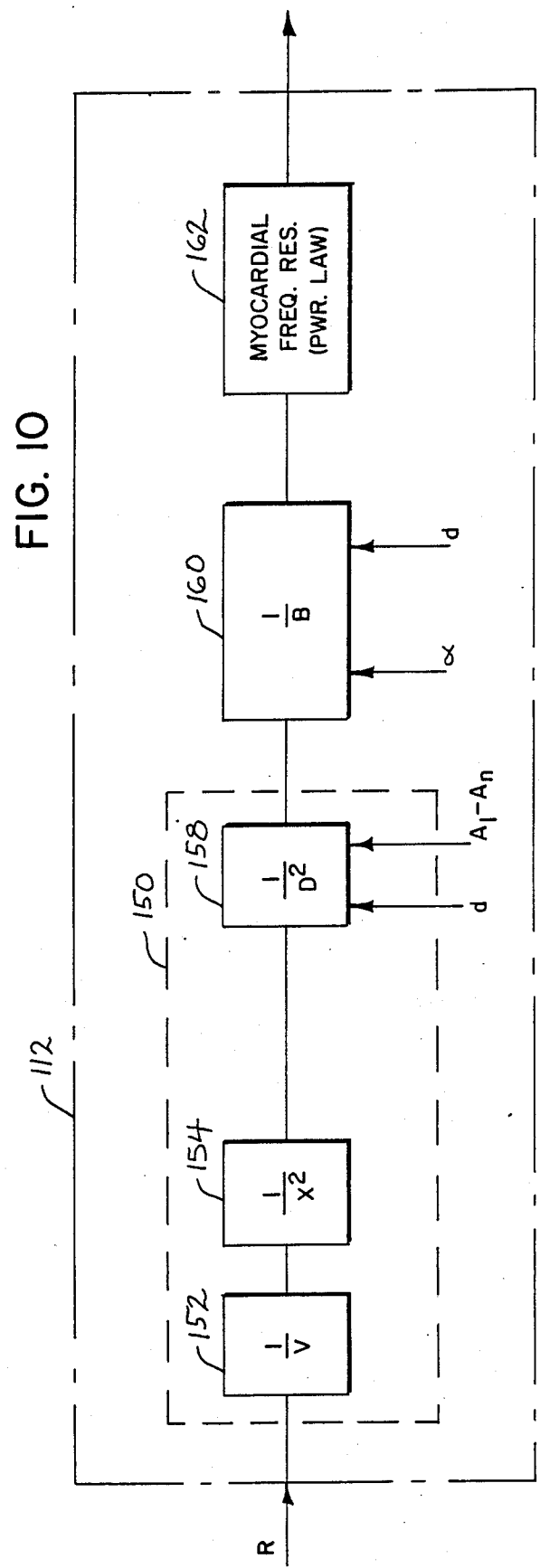

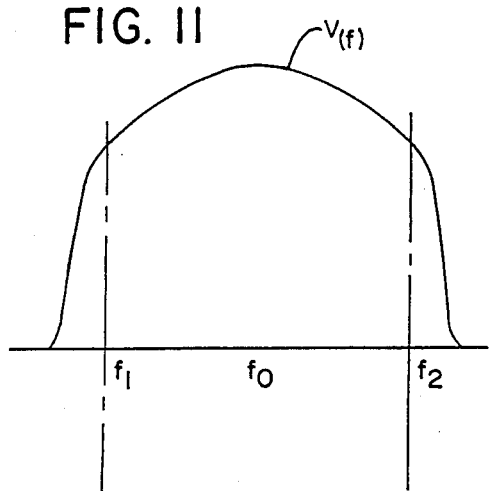
FIG. 11
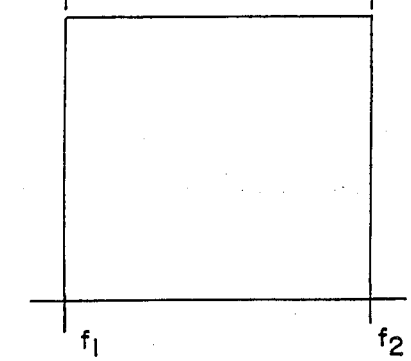
FIG. 11B
FIG. 11C
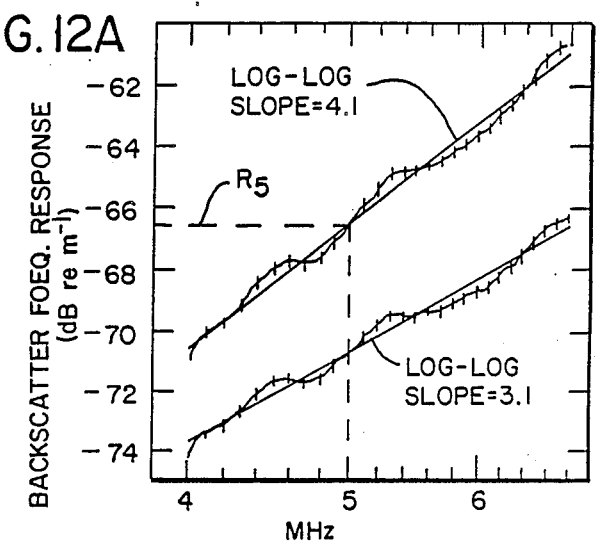
FIG. 12A
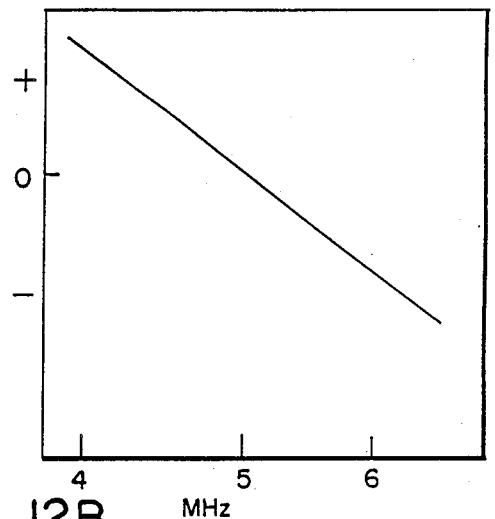
FIG. 12B
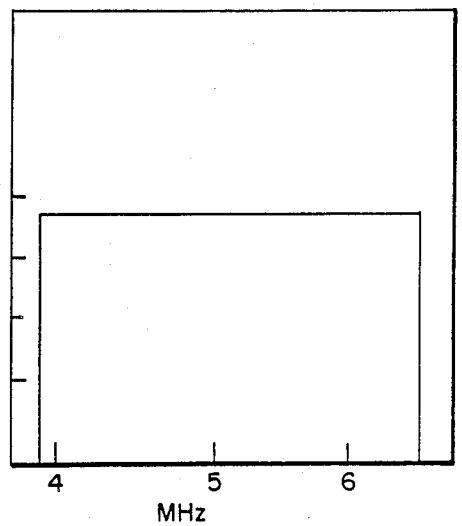
FIG. 12C

APPARATUS AND METHOD FOR OBTAINING ULTRASONIC BACKCATTER MEASUREMENT FROM TISSUE

The present application is a continuation application of U.S. patent application Ser. No. 055,732, filed May 29, 1987, and now abandoned.

BACKGROUND OF THE PRESENT INVENTION

The present invention is directed to an apparatus and method for obtaining measurement of the magnitude of ultrasonic random backscatter from tissue forming a region of distributed, unresolved ultrasonic reflectors. Such tissue may comprise that of the myocardium and differs from tissue forming a more highly resolved reflector, such as the mitral valve. More particularly, the present invention is directed to an apparatus and method for obtaining the optimal measurement of ultrasonic random backscatter magnitude from such tissue.

The optimal magnitude measurement is the maximum likelihood or minimum variance estimate of the magnitude.

The myocardium is the muscular wall of the heart. Through its contraction and relaxation, the heart is driven to pump blood through the circulatory system. Constrictions or obstructions in the blood vessels serving the heart muscle can result in a myocardial infarction or "heart attack" in which a volume of tissue is permanently injured by the circulatory loss. However, prior to infarction there may be a far greater tissue volume in which blood supply is already deficient. In this volume, the tissue has been damaged but the possibility exists for reversing, or at least stabilizing, the damage by appropriate rest, drug therapy, or surgery. Such tissue is termed "ischemic." With the recognition that myocardial infarction is a dynamic process, extensive efforts have been directed to protecting ischemic myocardial tissue in an effort to avoid or reduce infarction.

These efforts have been hampered by a lack of means to accurately and reliably determine the location and volume of ischemic tissue in the myocardium in order to quantify the injury.

Electrocardiography is of assistance in determining if heart muscle damage has occurred and the magnitude of the damage but is of limited assistance in mapping ischemic myocardial tissue. Angiography, in which a radio-opaque dye is injected in the coronory arteries can determine the location and extent of obstruction, but again, mapping of ischemic muscle is left somewhat to inference. There is also a medical risk to an already sick patient associated with angiography, particularly in the catheterization required to inject the dye.

As the result, other techniques have been sought to provide an accurate, reliable determination of the location and volume of ischemic muscle while reducing patient risk. Ultrasonic imaging presents one possibility. Ultrasonic imaging is a non-invasive and non-injurious diagnostic technique in which acoustic energy is applied to the body by an ultrasonic transducer. The returning backscatter or echo signals are received by the transducer, recorded, and analyzed. Because of its non-invasive nature and high level of safety, ultrasound has found considerable use in diagnostic procedures, as for example, viewing a fetus in utero or scanning the brain or breast for pathological conditions.

With respect to the application of ultrasound to cardiology, extensive use of echocardiography has been made in analyzing the operation of the mitral valve of the heart. The difference in the acoustic impedance between the blood filled heart chambers and the tissue of the valve forms a resolvable reflector for the ultrasonic energy. This makes for a distinct backscatter signal that is relatively easy to process and interpret.

The myocardium is considerably more difficult to image ultrasonically, since its tissue comprises a region containing, non-resolving reflectors or targets for the acoustical energy. Such a region has multiple, fine reflecting structures that produce multiple, fine echos that are individually unresolvable. Further, the individual elements of the fine, reflecting structure are spatially distributed. The returning signal is from a region rather than a well defined anatomical feature. Mathematical techniques must be utilized to deal with the random backscatter from such a region. Optimal techniques for ultrasonically examining the myocardium do not currently exist.

Certain ultrasonic random backscatter properties of myocardial tissue are known, as are the alterations in the random backscatter properties when the myocardial tissue is ischemic. Such properties and alterations include the following. First, the backscatter signal is amplitude modulated in accordance with the contractions of the myocardium. Specifically, the magnitude of the backscatter signal is greater when the myocardium is relaxed and decreases when the heart muscle contracts. Second, the magnitude of the amplitude modulation changes with ischemia. Specifically, the magnitude of the amplitude modulation becomes less with ischemia, i.e. there is a smaller difference between the peaks and valleys of the modulation. Also, there is a phase shift in the amplitude modulation with respect to the cardiac cycle with ischemia. Third, the magnitude of the backscatter signal, time averaged over a heart beat, is increased with ischemia.

The foregoing phenomena have been determined invasively as with the ultrasonic transducer applied directly to the myocardium. However, it can be readily appreciated that direct application of an ultrasonic imaging transducer to the heart muscle is ordinarily precluded from the medical and practical standpoints so that it is not possible to map ischemic myocardial tissue using its backscatter properties with this technique.

What is needed is a technique by which the magnitude of ultrasonic backscatter from the myocardium and its amplitude modulation and phase characteristics can be accurately obtained non-invasively, i.e. with the ultrasonic transducer applied to the external wall of the chest, rather than directly on the heart.

However, it will be appreciated that noninvasive imaging of the myocardium is considerably more difficult than direct, invasive imaging for a number of reasons. The parts of the body through which the ultrasonic signals must pass from the transducer on the chest to the myocardium in the thorax, and back, have a deleterious effect, often termed bulk tissue loss, on the echo signals received by the transducer. This is in addition to the effects of various aspects of the instrumentation, including the magnitude and frequency of the signal transmitted by the transducer, the frequency responses of the transducer and circuitry of the instrumentation, and the relationship of the transducer and target tissue, termed diffraction. The poor ultrasonic properties of the myocardium, described above, further complicates matters.

As a result, existing ultrasonic apparatus and methods fail to provide backscatter data from myocardium containing signal characteristics that are medically useful, for example, in diagnosing and mapping myocardial ischemia.

While the diagnosis and mapping of ischemia through the use of ultrasound has been discussed above, it will be appreciated that a technique for obtaining an optimal magnitude measurement would permit diagnosis of other cardiac conditions ultrasonically. For example, since amplitude modulation of the backscatter is due to the contraction of the heart muscle, close analysis of modulation data could allow determination of the state of contractility of the myocardium. Further, it would be highly desirable to use ultrasound to determine the condition of other tissue besides that of the heart, that also forms an unresolved ultrasonic reflector. Such tissue might include glandular organs, such as the liver or pancreas.

SUMMARY OF THE PRESENT INVENTION

The present invention is thus directed to an apparatus and method for obtaining a measurement, and particularly the optimal measurement, of ultrasonic random backscatter magnitude from a region of distributed, unresolved ultrasonic reflectors when the transducer is applied in a non-invasive fashion, i.e. to the exterior of the body. In connection with the myocardium, the backscatter measurement, so obtained, provides an optimal measurement of the magnitude and amplitude modulation characteristics needed to detect the ischemic or contractile condition of the myocardium.

The optimal measurement may be carried out in a reliable and rapid manner. With respect to myocardial examination, the non-invasive nature of the present invention permits such examination to be carried out immediately after infarction has occurred, on critically ill patients, and with the convenience of a bed side modality.

In obtaining the magnitude of ultrasonic random backscatter, the present invention teaches as follows. From a mathematical and physical analysis of the ultrasonic backscatter from a tissue region of distributed, unresolved reflectors such as the myocardium, it has been determined that the frequency spectrum of the backscatter subscribes to the power law, more particularly to that expression of the power law termed Rayleigh scattering in which the intensity of the backscatter is proportional to its frequency to the fourth power. It has also been determined that the intensity of the myocardial backscatter signal is a random variable with a chi-square characteristic. These features permit the intensity of myocardial backscatter to be optimally determined by whitening the received signal, squaring it, and summing it.

The optimal measurement of ultrasonic random backscatter is obtained by band limiting and by whitening the received signal in a prescribed manner prior to squaring, summing and by hereinafter noted specified scaling. Specifically, the whitening is to be carried out for all spectrally altering factors to which the ultrasonic signal has been subjected. This includes whitening for the power law frequency response characteristics of the myocardium itself. Spectral whitening is also carried out for the frequency response effects of instrumentation, including the transmitted signal, transducer, and diffraction. Spectral whitening is further provided for bulk tissue loss.

The signal, so whitened, is squared and integrated and a signal indicative of the power of the received signal obtained therefrom as by dividing the integration interval. To obtain the optimal backscatter measurement, it is necessary to scale the power signal by a factor accounting for the energy of the effective transmitted ultrasonic signal and by a factor providing appropriate units of measurement.

The result is the minimum variance, or optimal measurement, of the ultrasonic random backscatter from the tissue, such as the myocardium. This optimal measurement may be time averaged over one or more heartbeats for use in the diagnosis of ischemia or other cardiac conditions. It may be subjected to discrete Fourier transform analysis, to obtain its amplitude modulation and phase characteristics for similar purposes.

DESCRIPTION OF THE DRAWING

The invention will be further understood by reference to the following detailed description taken in conjunction with the drawing.

In the drawing:

FIG. 9 is a detailed schematic diagram of the input circuitry of the apparatus of the present invention.

FIG. 10 is a detailed schematic diagram of the whitening filter of the apparatus.

FIGS. 11A–C are graphs showing whitening of the received ultrasonic backscatter signal with respect to the frequency spectrum of the transmitted ultrasonic signal.

FIGS. 12A–C are graphs showing whitening of the received ultrasonic backscatter signal with respect to the frequency response of the myocardial tissue.

DETAILED DESCRIPTION OF THE PREFERRED EMBODIMENT

While the following detailed description contains reference to certain dimensions, units or quantities as an aid to understanding the invention, it must be clearly understood that such recitation is for exemplary purposes only and not in limitation of the scope of the invention. Further, while the invention is described in connection with the imaging of the myocardium, it will be appreciated that it can be used, with any appropriate modification, in the imaging of other tissues.

Figure 1:
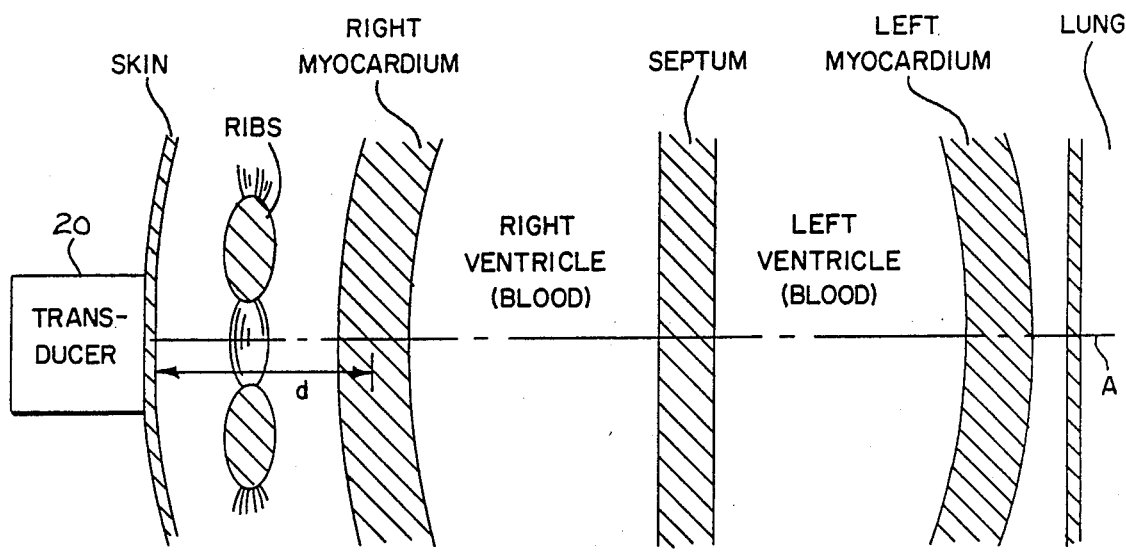
FIG. 1. is a somewhat schematic, cross-sectional view of the anatomy of the chest in a plane parallel to the sagittal plane of the body.

FIG. 1 shows ultrasonic imaging of body tissue, for example the heart. Ultrasonic transducer 20 is applied to the wall of the chest to transmit an ultrasonic signal into the chest along axis A and to receive the reflected backscatter.

The transmitted signal is usually a pulse signal of desired frequency and duration. A typical echocardiographic signal might be an acoustical pulse ½ microseconds in duration and 3 MHz in frequency. While the frequency of the signal is in a range commonly termed "radio frequency" or "RF", the signal is not a radio or electromagnetic signal. It is an acoustical signal.

The transmitted ultrasonic signal passes through the skin and the muscle between the ribs to the myocardium of the right wall of the heart. In the example shown, it then passes through the blood in the right ventricle, the septum between the chambers of the heart, the blood in the left ventricle, to the myocardium of the left heart wall. It thereafter continues through other organs, such as the lung, not here pertinent.

Figure 2A:
FIG. 2A is a graph schematically showing an ultrasonic RF backscatter signal produced by the anatomy of FIG. 1.

Following transmission of the ultrasonic signal, transducer 20 switches to the receive mode and begins to receive the backscatter or echo signal from the tissue of the thorax. FIG. 2A shows the RF acoustical echo signal received by transducer 20, including portions RM and LM comprising the backscatter from the myocardium of the right and left heart walls. FIG. 2A shows the distinct backscatter produced by points of marked difference in acoustical impedance, such as that existing between the myocardium and the blood. It also shows the indistinct backscatter from an unresolved ultrasonic reflecting region such as the myocardium. FIG. 2A further shows the attenuation of the ultrasonic signal with axial distance, i.e. the received signals from left myocardium are weaker than those from the right myocardium due to the greater amount of tissue that must be traversed by the signals of the left myocardium to and from transducer 20. In an actual signal, the amount of attentuation would be far greater than that graphically shown in FIG. 2A.

Assuming a velocity of sound in tissue of approximately 1500 meters per second, it would take about 260 microseconds for the acoustical pulse to travel to the left myocardium and return to transducer 20 for a typical heart that is 20 cm in size. Transducer 20 could then generate another pulse to obtain a signal for a subsequent time in the cardiac cycle, to use a different frequency, to shift axis A, or for other reasons. The result would be a further backscatter signal similar to FIG. 2A.

Figure 2B:
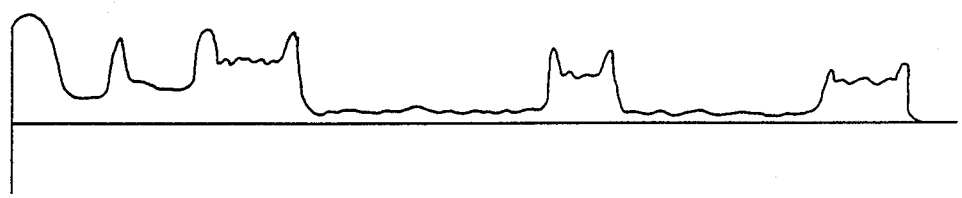
FIG. 2B is a graphic representation of an oscilloscopic display of the signal in FIG. 2A, the showing of FIG. 2B comprising an envelope signal with time gain compensation.

In order to obtain diagnostically useful information from the RF signal in FIG. 2A, it is conventional to convert the acoustical signal to an electronic signal for signal processing by analog or digital means. The electronic signal may be displayed on a cathode ray oscilloscope. FIG. 2B shows a typical oscilloscopic signal with basic signal processing. FIG. 2B shows the video envelope of the RF signal of FIG. 2A. The enveloping process outlines the magnitude of the RF signal. The signal in FIG. 2B is also time or range gain compensated. That is, the backscatter originating from further into the thorax along axis A is amplified to a greater extent than backscatter originating closer to the transducer. This helps to overcome the attenuation of signals originating more deeply in the chest.

Figure 3A:
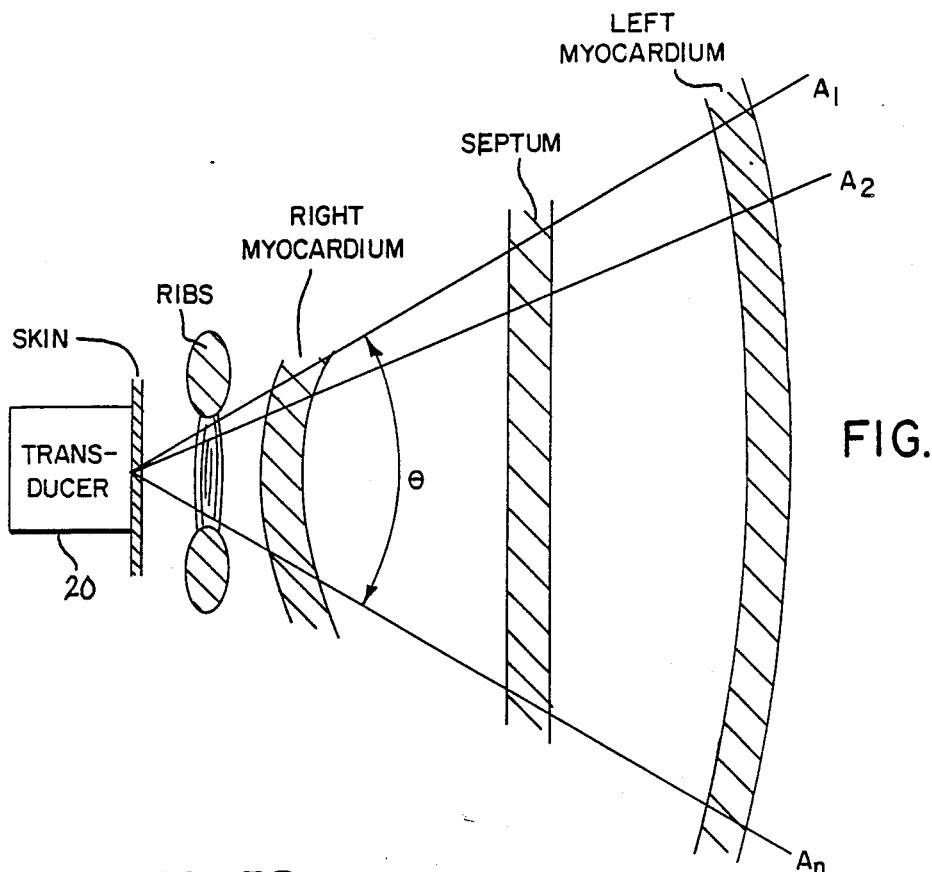
FIG. 3A shows ultrasonic scanning of the heart.
Figure 3B:
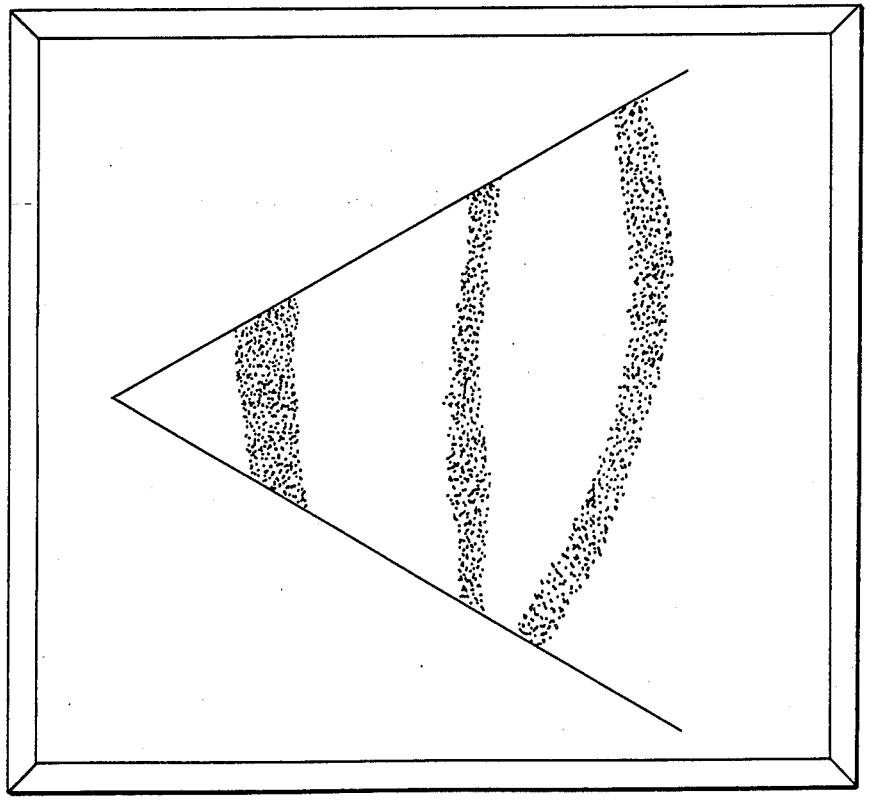
FIG. 3B shows a video image produced from the scanning of FIG. 3A.

Another technique for displaying echocardiographic information is shown in FIG. 3 and employs a video monitor. It will be appreciated that while ultrasonic backscatter data obtained along a single axis, such as axis A, shown in FIG. 1 may be useful for some types of diagnostic work, for mapping the ischemic condition of the heart, a volume of the heart must be ultrasonically scanned. For this purpose, transducer 20 may be angularly moved about an axis normal to the plane of the paper in FIG. 1 to swing the axis of signal generation, as shown in FIG. 3A. An ultrasonic pulse is transmitted along an axis $A_1$ and the backscatter signal recorded. Transducer 20 is then arcuately moved to axis $A_2$, an ultrasonic pulse transmitted and backscatter signal recorded along an axis $A_2$, and so on through axis $A_n$ as the transducer moves through angle $\theta$. The backscatter signals along the various axes may be conveniently recorded or stored in a digital memory device, such as that of a digital scan converter. The signal characteristics for each increment of time, or corresponding distance d, along each of the axes A are recorded in the memory device. Distance d is shown in FIG. 1 for clarity. The recorded backscatter data is read out of the memory device in an appropriate sequence and used to modulate the electron beam in the monitor at each picture element (pixel) of the screen of the monitor to create the display shown in FIG. 3B.

It will be appreciated that while transducer 20 has been described as being physically moved, supra, transducer 20 may more typically comprise phase arrayed elements in which a plurality of transducer elements are electronically switched to direct them along the various axes.

Further, it will be appreciated that while a single scan has been described above, the video image would more typically be formed using averaged data from a plurality of scans, for example, twenty scans so as to provide a signal typifying the physiological condition of the heart. The data from the plurality of scans would be stored in the digital memory and averaged to provide the data supplied to the video monitor.

At conventional imaging frequencies, the image of FIG. 3B on the video monitor provides the physician with an essentially instantaneous ultrasonic picture or "snapshot" of the portion of the heart being scanned by transducer 20 at one particular instant in the cardiac cycle. To further assist the physician, it is desirable to provide a series of images showing the heart at a plurality of points during the cardiac cycle. For example, eight image points may be established at the beginning of eight equal time increments of the cardiac cycle. Ultrasonic imaging data is obtained at each image point in the manner described above and the image at each of the points sequentially presented on the video monitor. The physician thus observes eight different "snapshots" of the condition of the heart at eight time spaced image points during each cardiac cycle. This technique is often termed "cine-looping" and is presented in "slow motion" with respect to real times in the cardiac cycle.

However, as noted supra, with conventional ultrasonic signal processing, the magnitude or amplitude modulation properties of the backscatter signal portions originating in the myocardium are not defined in the processed signal with sufficient accuracy to be useful in diagnosing ischemia or other conditions of the myocardium. Further, conventionally used signal processing techniques beyond the enveloping and time gain compensation described above, tend to reduce the usefulness of conventional backscatter signals for this purpose even more. For example, because of the attenuation of the RF signal, the backscatter has a wide range of signal magnitudes. This makes it necessary to consider some form of dynamic range compression. This compression is often non-linear in nature. As a result of such compression techniques, the ability to obtain the absolute magnitude of the backscatter and relative relationships between signal magnitudes, both of which are needed for ischemia diagnosis, is further lost.

FIG. 4 shows the backscatter signal data desired from the myocardium, as heretofore determined from invasive investigation of the myocardium. FIG. 4A shows, for reference purposes, the well-known electrocardiographic wave form associated with the periodic operation of the heart, including the prominent QRS feature. FIG. 4B shows blood pressures in the heart produced by contraction of the myocardium as a result of the electrical stimulation shown in the electrocardiographic wave. The left ventricular pressure is used for illustrative purposes. Following stimulation of the myocardium by the QRS signal of the electrocardiogram, the myocardium contracts at time $T_b$, resulting in an increase in blood pressure in the chambers of the heart. This period commencing with the contraction of the myocardium through its subsequent relaxation at time $T_r$ is the systole of the heart muscle. The muscle remains relaxed during the diastole until a subsequent excitation at time $T_{b1}$. The time between $T_b$ and $T_{b1}$ comprising a cardiac cycle is approximately 900–1000 milliseconds for a normal heart rate.

Figure 4A:
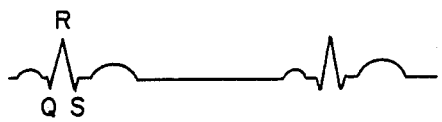
FIG. 4A is an electrocardiographic wave form showing the QRS complex that excites the heart muscle to contract.
Figure 4B:
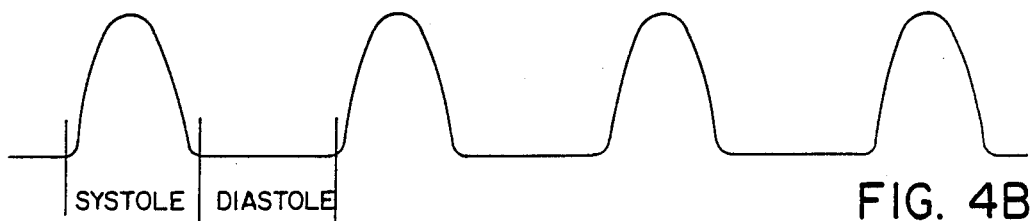
FIG. 4B is a wave form showing fluid pressure produced in the heart by contraction of the heart muscle.
Figure 4C:
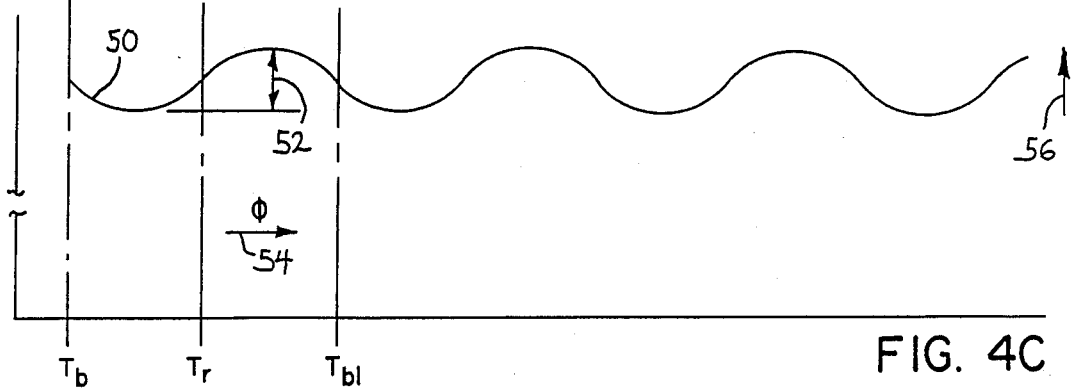
FIG. 4C shows, in generalized form, ultrasonic phenomena associated with the myocardium.

FIG. 4C shows, in a highly schematic form, the random backscatter properties of the myocardium as related to the cardiac cycle, as learned from a series of invasively obtained backscatter signals of the type analogous to those shown in FIGS. 2A and B obtained sequentially, at intervals, throughout the cardiac cycle for a particular volume of myocardial tissue. For example, the backscatter signal data at time $t_i$ in FIG. 2A, from each of a sequence of signals obtained during the course of a cardiac cycle may be used. This backscatter signal data is that originating in the right myocardium at the distance d from the transducer shown in FIG. 1. The backscatter signal magnitudes, averaged over a number of cycles, are used to construct the graph of FIG. 4C.

The amplitude modulation of the backscatter signal in accordance with contractions and relaxations of the myocardium is shown by the undulating character of graph 50. The magnitude of the backscatter 50 decreases during the contractions of systole and increases in the relaxation of diastole. With ischemia of the myocardium, the magnitude of the amplitude modulation will decrease. That is, there will be a smaller difference 52 between the peaks and valleys of the modulation. There will also be a shift in phase $\phi$ in the amplitude modulation with respect to the cardiac cycle. This can be visualized as a left or right translation of the graph of FIG. 4C with respect to the cardiac cycle of FIG. 4B, shown by arrow 54. The magnitude of the backscatter signal, when time averaged over the cardiac cycle is increased with ischemia. This may be visualized as translating the graph of FIG. 4C upwardly on a time averaged basis along the ordinate of FIG. 4C as indicated by arrow 56.

Figure 4D:
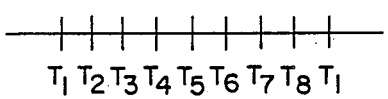
FIG. 4D shows the establishment of image points in the myocardium.

FIG. 4D shows image points $T_1$–$T_8$ that may be used to provide a cine-loop of images in the cardiac cycle. The image points are about 125 milliseconds apart for a normal 1000 millisecond heart rate.

Figure 5:
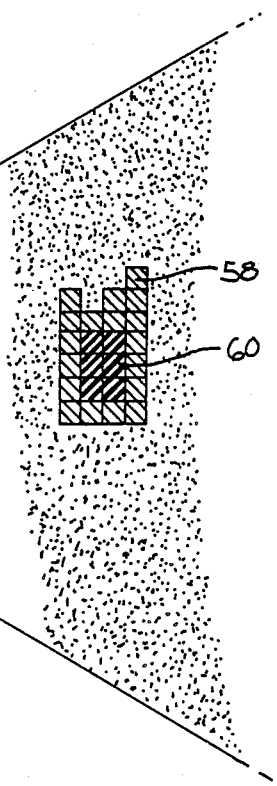
FIG. 5 shows a video image that may be produced by the apparatus of the present invention.

As noted above, the apparatus and method of the present invention optimally obtains the amplitude modulation and magnitude characteristics of the backscatter signals so that they can be quantitatively analyzed and used to determine ischemia or other image such as that shown in FIG. 5 in which areas of altered backscatter magnitude or amplitude modulation are indicated, as an aid to diagnosing ischemia, loss of contractility, or other conditions. Color scales may be used for this purpose, in the same manner as in computerized tomographic x-ray images or nuclear magnetic resonance images. For example, the enlarged image shown in FIG. 5 show backscatter amplitude modulation characteristics of the right myocardium. The image may include pixel areas 58 and 60 highlighted to varying degrees, depending upon the amount of amplitude modulation decrease. Areas indicated in darker tones represent areas of greater decrease in amplitude modulation and a higher degree ischemia. As noted above, the presentation of the backscatter data would typically be in a cine-loop, showing the amplitude modulation conditions of the myocardium at various image points in the cardiac cycle.

In the same manner, an amplitude modulation phase image or a backscatter time averaged magnitude image could be presented to the physician.

In order to obtain the optimal measurement of random backscatter magnitude so as to be able to present backscatter data in the manner shown in FIGS. 3B and 5, or otherwise, it is necessary to ascertain the scattering properties of the myocardium, including its frequency response and statistical properties. In accordance with the teaching of the present invention, as experimentally determined and verified, the frequency response characteristics of the myocardial scattering subscribe, in close approximation, to the power law, and more particularly to that expression of the power law in which the power is four. This makes the myocardial scattering Rayleigh in nature. In Rayleigh scattering, the intensity of the scattered energy is inversely proportional to the fourth power of the wavelength of the energy or, conversely, the intensity of the scattered energy is directly proportional to frequency to the fourth power. A more workable expression is to convert intensity to magnitude by reducing the exponent to 2, i.e. the square, and to provide a constant so that the expression becomes one of equality rather than proportionality. The power law and Rayleigh scattering state that the magnitude of the scattered energy is equal to a constant times the frequency squared.

Figure 6:
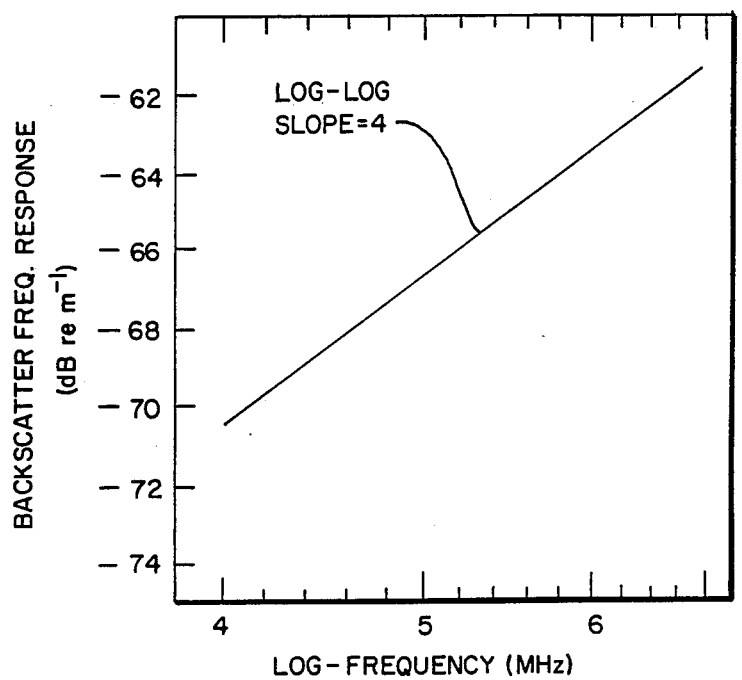
FIG. 6 is a graph showing the ultrasonic frequency response characteristics of the myocardium.

When graphed on log - log coordinates, i.e. log of frequency on the abscissa and log of magnitude on the ordinate, the result is the straight line shown in FIG. 6. This graph shows the idealized frequency response of the myocardium. It will be appreciated that the actual frequency response will vary to some degree from the idealized showing of FIG. 6.

That the properties of the ultrasonic backscatter signal of the myocardium subscribe to the power law and comprise Rayleigh scattering was determined by invasive measurements on the myocardium with all factors other that myocardial frequency frequency response either eliminated or knowingly compensated for.

Once the frequency response characteristics of the myocardium are known, it is necessary to test for the statistic of the signal in order to provide a technique for producing an optimal estimate. This is due to the random nature of the backscatter. By analysis and experimentation, it was determined that the intensity of the myocardial backscatter signal is a random variable with a chi-square statistic. This being established, in accordance with the statistical theory of communication, the maximum likelihood estimate of the intensity of myocardial backscatter can be obtained by spectrally whitening the backscatter signal, squaring the whitened signal, and integrating the squared signal.

Figure 7:
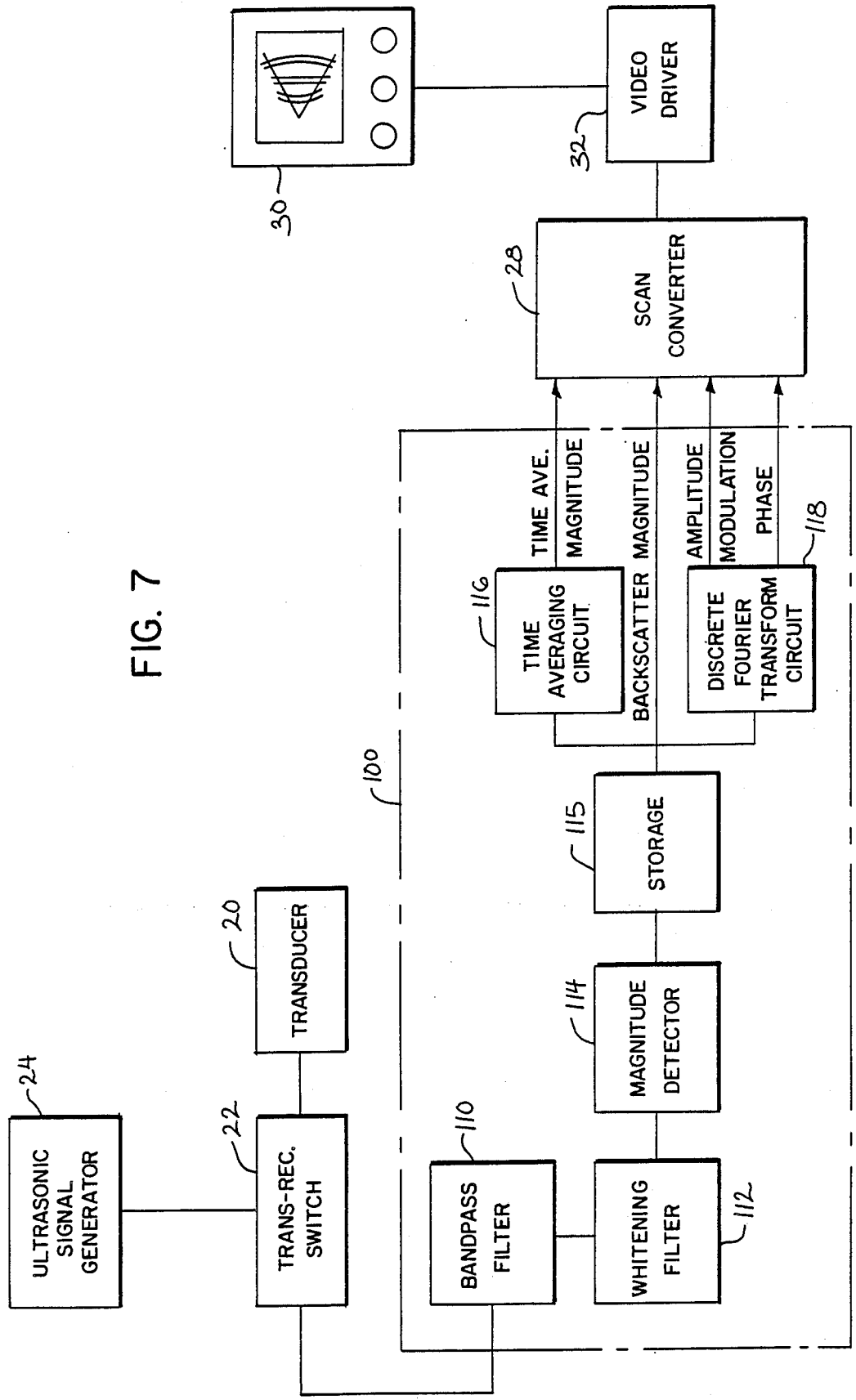
FIG. 7 is a schematic diagram of an ultrasonic scanner incorporating the apparatus of the present invention.
Figure 8A:
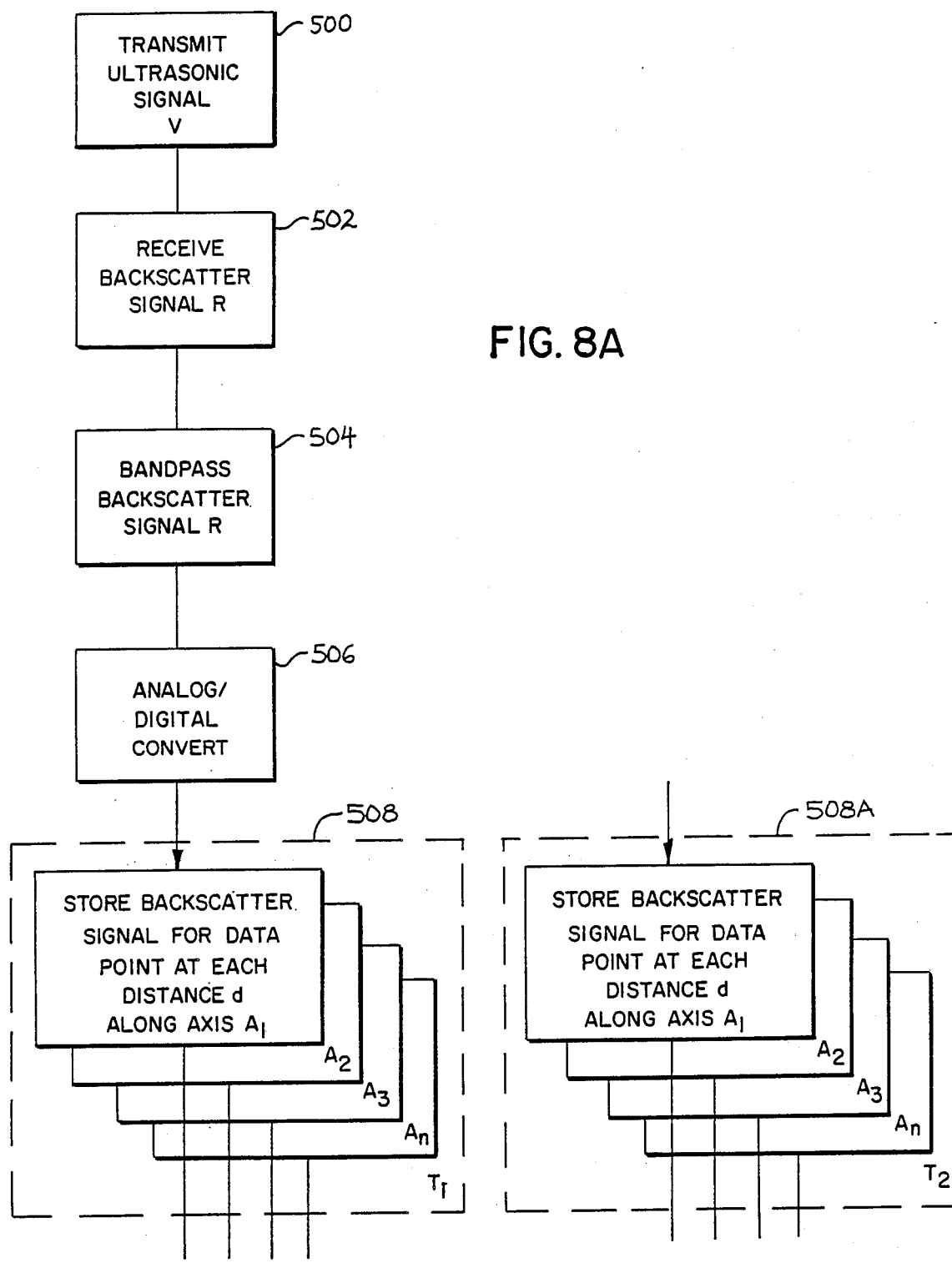
FIGS. 8A through 8D are block diagrams illustrating the technique of the present invention.
Figure 8B:
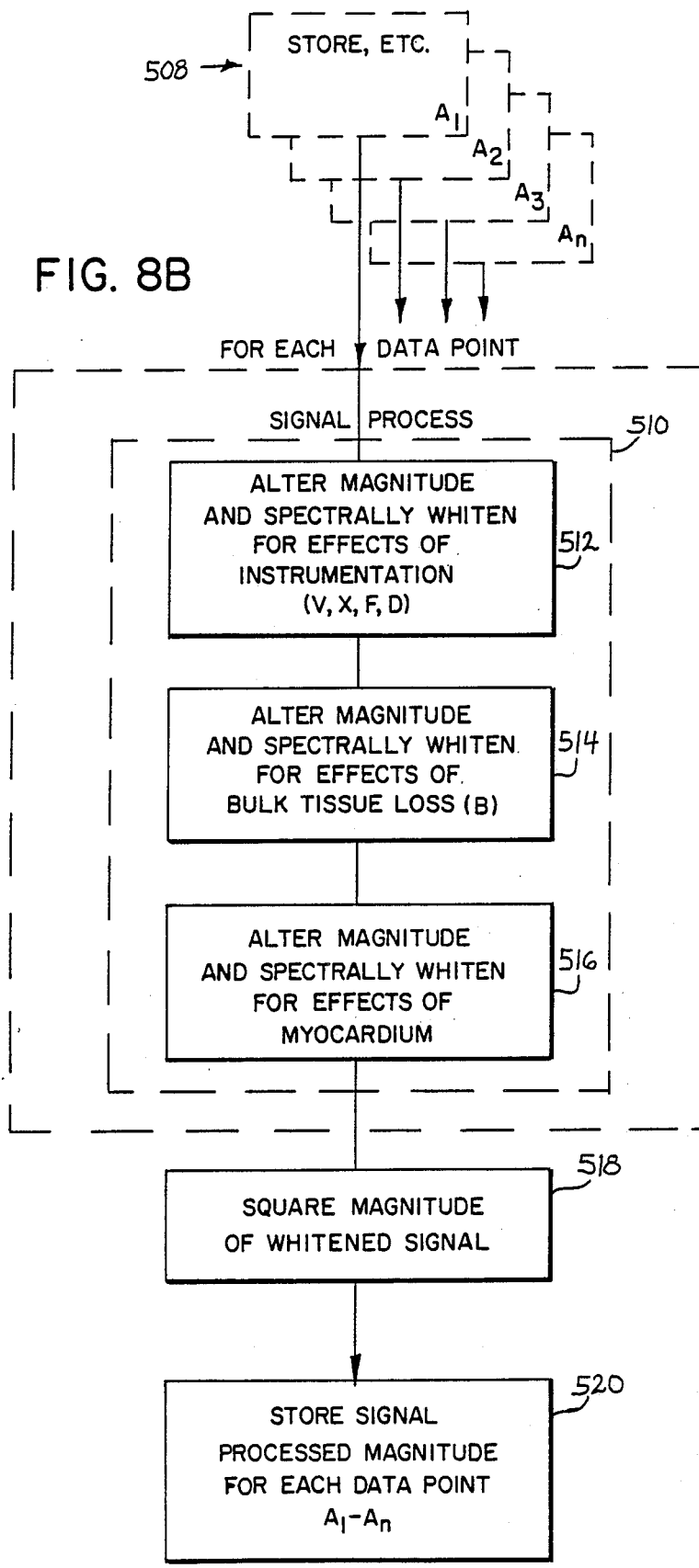
Figure 8C:
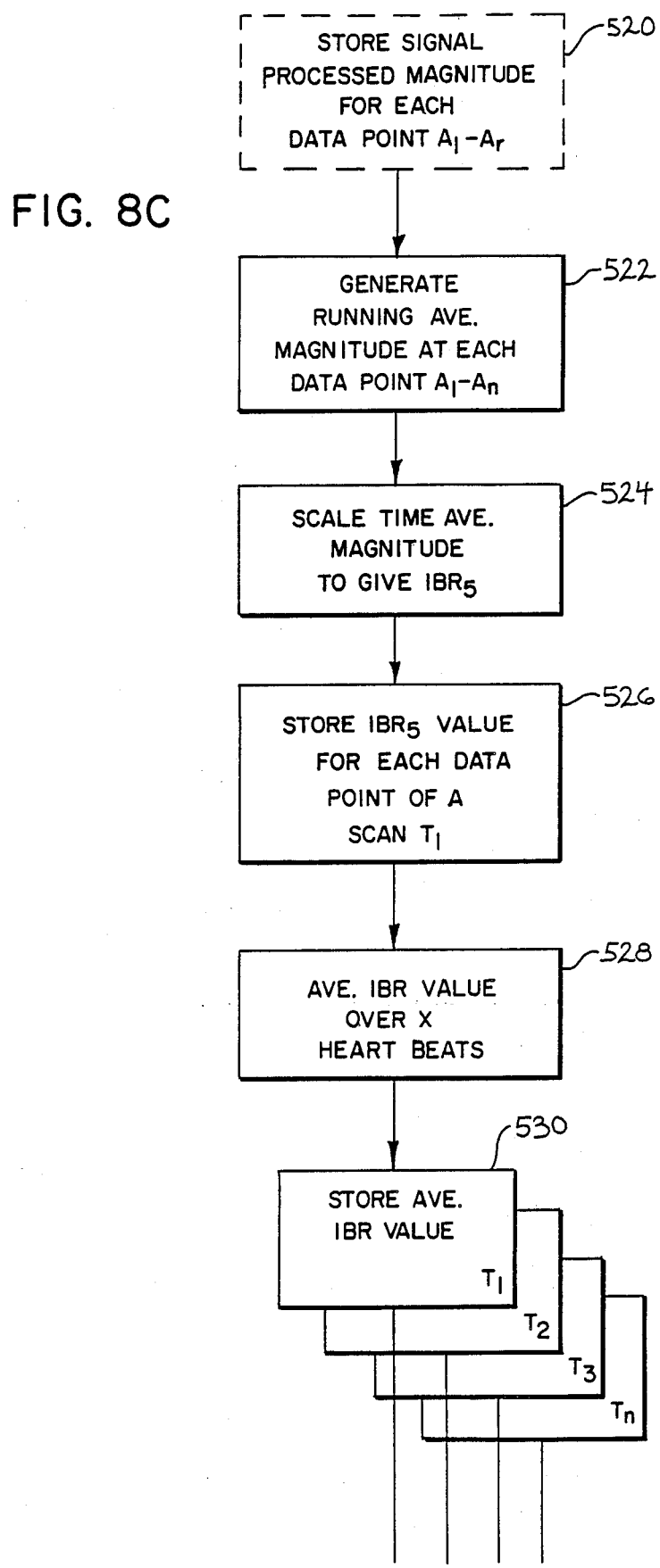
Figure 8D:
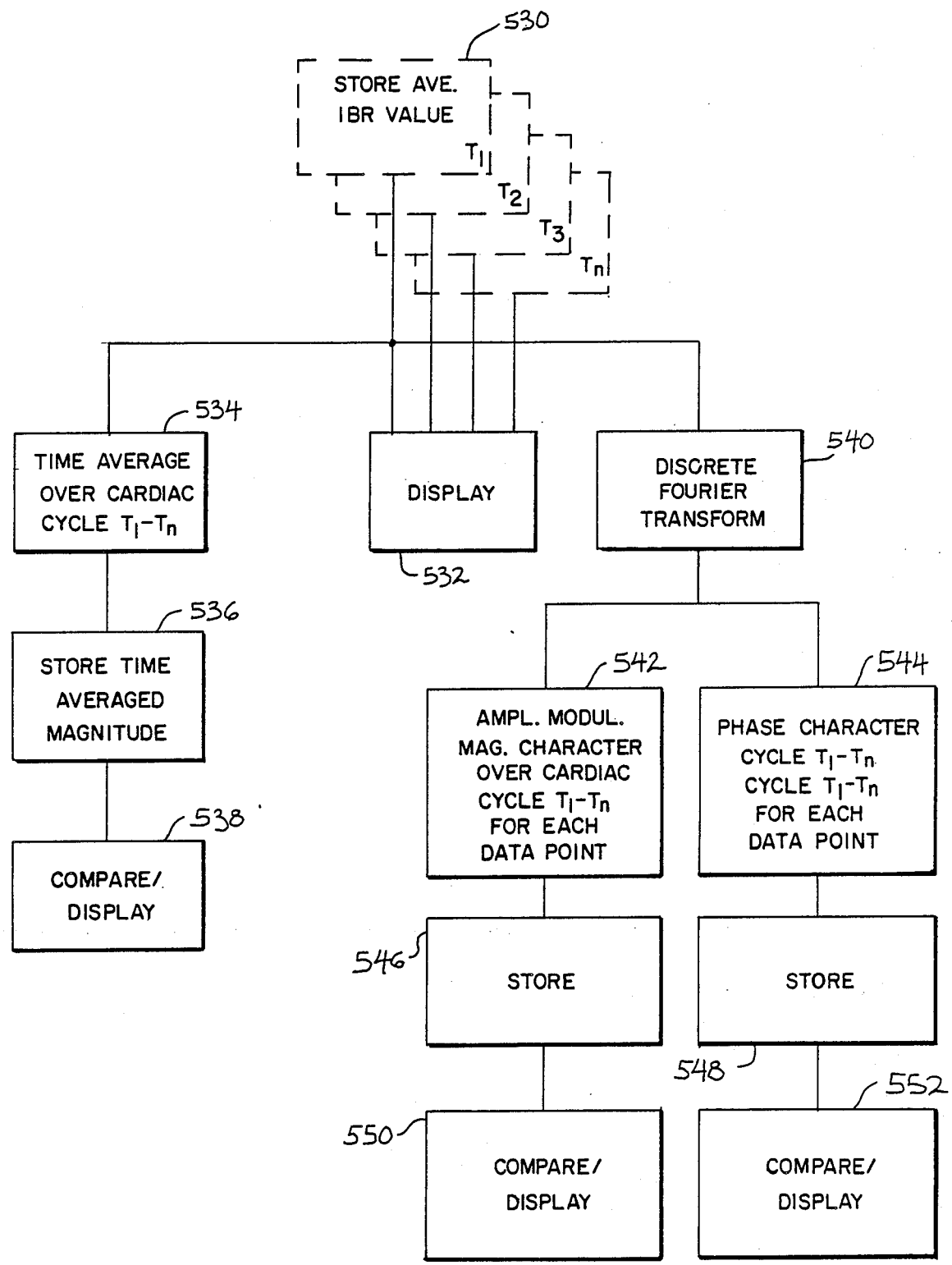

FIG. 7 shows, in generalized block diagram form, circuitry for obtaining the optimal measurement of myocardial backscatter in accordance with the present invention, and for producing images of the type described above. FIG. 7 shows transducer 20 connected through transmit/receive switch 22 to ultrasonic signal generator 24. Transducer 20 is typically of the piezoelectric crystal type. Apparatus 100 of the present invention is connected to transmit/receive switch 22 to receive the backscatter signal from the tissue undergoing ultrasonic examination. Apparatus 100 provides the necessary signal processing to the backscatter signal so that signals stored in digital scan converter 28 may generate displays of the type shown in FIGS. 3 and 5 on the screen of video monitor 30 driven by video driver 32. The circuitry of apparatus 100 may comprise analog elements, digital elements, or a combination of both. However, apparatus 100, will typically comprise, in great measure, digital elements and is described as such below. When so formed, apparatus 100 may, in practice, be combined with digital scan converter 28. However, apparatus 100 is shown separately in FIG. 7 to facilitate explanation.

Apparatus 100 includes input circuitry 110 shown in detail in FIG. 9 including a band pass filter to remove noise from the received backscatter signal. The signal is then provided to whitening filter 112. The term "whitening" refers to the production of a flat or constant frequency spectrum over the frequency band established by filter 110. The term was adopted by analogy to a "white" object. A white object, such as snow, is one that reflects all visible frequencies of light in the same proportion, making it appear "white" to the eye. The operation of a "whitening" filter is analogous.

In apparatus 100, whitening filter 112 whitens the band passed received signal to overcome spectral alteration of the signal in the course of its generation, passage through body tissue, reflection off the target and reception so that the output of the filter is spectrally white. The specific factors producing spectral alteration of the backscatter and for which whitening must be provided are described in connection with the mathematical treatment below and in FIG. 10.

Figure 13:
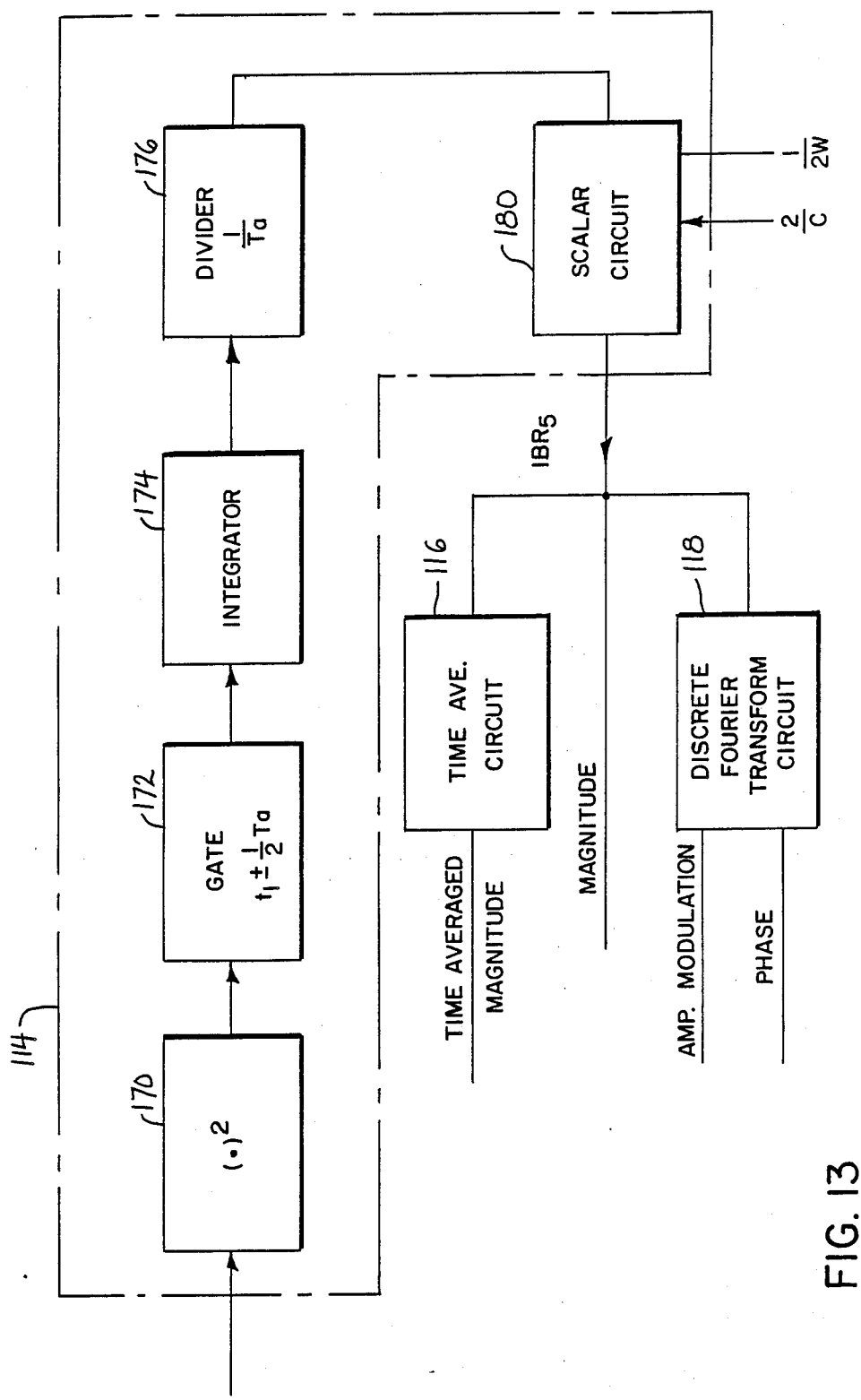
FIG. 13 is a detailed schematic diagram of the magnitude detector of the apparatus of the present invention.

The output of whitening filter 112 is provided to magnitude detector 114, shown in detail in FIG. 13, that detects, by summing and integrating, the power of the received signal output of whitening filter 112 and provides appropriate scaling.

The output of magnitude detector 114 is the magnitude of the random ultrasonic backscatter from the myocardium and may be stored in signal storage device 115. The output of magnitude detector 114 may be provided to time averaging circuit 116 to provide the magnitude of the backscatter, time averaged over the cardiac cycle useful in diagnosing ischemia or other conditions.

The output of magnitude detector 114 may be applied to discrete Fourier transform circuit 118 that extracts the amplitude modulation and phase characteristics of the output of magnitude detector 114.

The outputs of apparatus 100 are provided to scan converter 28 for storage purposes and to provide signals to video driver 32 for generating video images on monitor 30, such as that shown in FIG. 5.

The present invention may be further appreciated by reference to the block diagram of FIGS. 8A through 8D showing the general manner in which same is carried out. An ultrasonic pulse signal, designated V is transmitted by transducer 20 as noted in block 500. While the ultrasonic pulse will have some nominal frequency of, for example, 3 MHz, it will be understood that a pulse type signal actually comprises a spectrum or bandwidth of frequencies both higher and lower than the nominal frequency. In the above example, the frequency spectrum or bandwidth of the transmitted signal may be 2 MHz.

Apparatus 100 receives the backscatter signal, designated R, from transducer 20 as noted in block 502. As hereinafter noted in detail, the received signal R will have the same spectrum or bandwidth of frequencies as the transmitted signal V. On a time or distance basis, received signal R will resemble that shown in FIG. 2A and contains the backscatter received from the tissue reflectors located along axis A. The received backscatter signal is band pass filtered as at 504 to remove noise. The frequency band passed by the filter may typically be 2 MHz wide and include the nominal frequency of the transmitted ultrasonic pulse V. Thereafter, in a typical practical embodiment of the present invention, the received signal is converted from analog to digital form at 506. The sampling rate employed may, for example, be 4 MHz, with each sampling forming a data point along the axis A. The backscatter signal data for the incremental distance d of each data point along a given axis A is stored in a memory device at 508.

The process is then repeated for each of the axes used in the scan so that the data for each data point along each axis $A_1$ through $A_n$ is stored in digital form, as shown at 508 in FIG. 7A. Block 508 presents the raw data for one "snapshot" or image of the type shown in FIGS. 3 and 5 at one image point, for example $T_1$, in the cardiac cycle. For a cine-loop, the entire process described above is repeated for the other snapshot-like images at the other image points in the cine-loop, as indicated by 508A.

Thereafter, the stored data for each data point is signal processed at 510 in accordance with the present invention to spectrally whiten the data to overcome the effects of spectral alterations in received signal R. Specifically, and as noted in detail below, the received signal R is spectrally whitened, as at 512, for the effects of the instrumentation of the circuitry shown in FIG. 6. These instrumentation effects include those arising from the spectral content and other characteristics of the ultrasonic signal V generated by generator 24 and transmitted by transducer 20. They also include the transfer function or frequency response X of tranducer 20 and filtering action or frequency response F of the circuitry of the instrumentation. Also included are the effects of diffraction. Diffraction D refers to the spectral alteration of the received signal occurring from the spatial relationship between transducer 20 and the reflecting tissue forming the target for the ultrasonic signal V.

In addition to instrumentation effects, it is also necessary to spectrally whiten at 514 to remove the effects of the bulk tissue loss B. This is the attenuation and spectral distortion arising from the tissue through which the ultrasonic signal must pass to and from the ultrasonic reflector of interest.

Finally in accordance with the teaching of the invention, it is necessary to spectrally whiten at 516 for the frequency response effects of the tissue, such as the myocardium, forming the ultrasonic reflector of interest.

Following the whitening of the ultrasonic backscatter signal, detection of the magnitude of the whitened signal is carried out. For this purpose, the magnitude of the processed signal at each data point is squared, as at 518, and stored as at 520.

The integration of the squared signals provides an indication of the power of the received signal R needed to provide the optimal backscatter measurement. The integration process may be considered as the generation of a running average magnitude for each data point in the scan, as at 522. The running average for each data point such as that at $t_i$ in FIG. 2 may be obtained by summing or integrating, the data from that point for example $t_i$ in FIG. 2a and from a predetermined number of preceding and succeeding data points in the averaging time $T_a$. The integrated quantity is then divided by the total number of data points used.

The running average magnitude at each data point is scaled by factors relating to the energy of the effective transmitted pulse signal and provide more useful dimensions at 524. The result is the maximum likelihood estimate of the ultrasonic random backscatter magnitude at each data point. As hereinafter noted this magnitude may be termed IBR5, that is, the integrated backscatter Rayleigh at 5 MHz. This value for each data point in the scan is stored at 526.

Thereafter, the stored IBR values are averaged over a desired number of heart beats as shown by 528 to render the values representative and stored as at 530.

The same procedures are followed for the scans occurring at other image points, $T_1$, $T_2$, . . . $T_n$ in the cardiac cycle, also as shown at 530, so that the magnitude of the random backscatter is obtained for all data points in each image.

The backscatter magnitude data obtained for each data point, as described above, may now be used for diagnostic purposes and to generate video images of the type shown in FIGS. 3 and 5, if desired. Thus, a map of the backscatter magnitude over the scanned portion of the heart may be obtained and displayed, as at 532, in cine-loop or other desired manner.

Or, the magnitude values may be time averaged over the cardiac cycle at 534 and stored at 536. The time averaged data is compared at 538 with base line data to ascertain shifts in time averaged backscatter magnitude, such as that shown by the arrow 56 in FIG. 4C that would indicate ischemia or other pathological conditions.

The stored average IBR values for $T_1$ through $T_n$ may be subjected to a discrete Fourier transform, as at 540, that extracts the amplitude modulation characteristic over the cardiac cycle, as at 542, and the phase characteristic, also over the cardiac cycle, as at 544. These values are stored, as at 546 and 548, respectively, compared with base line data at 550 and 552, and used to generate a video display. The comparison of the amplitude modulation characteristic shows the change indicated by the arrow 52 in FIG. 4C. The comparison of the phase characteristic shows the change indicated by the arrow 54 in FIG. 4C.

While the foregoing has described the use of video images, it will be appreciated that the information obtained from the above-described technique may be presented in tabular or other form.

The manner in which the the spectral whitening is carried out, as well as the basis on which the scaling required to obtain an absolute measurement value is carried out will be appreciated from the following mathematical treatment of ultrasonic backscatter measurement.

Ultrasonic backscatter measurement is mathematically summarized in the ultrasonic equation, forming equation 1, below. Equation 1 computes the received signal spectrum R from a point scatterer excited by a single transducer system. The quantity $\omega$ is a variable indicative of frequency. The quantity u is a factorial indicating the location of the point scatterer in the transducer field. The quantity d is the distance from the transducer to the point scatterer.

$$R(\omega)=(\tfrac{1}{2})V(\omega)X^2(\omega)F(\omega)B((\omega,d)D^2(\omega,u)Y_oS(-\omega,u)e^{-j\omega T d} \qquad (1)$$

In equation 1, V is the transmitted signal spectrum. The factor of $\tfrac{1}{2}$ indicates that $\tfrac{1}{2}$ of the open circuit voltage V of a controlled impedance transmitter would be returned by a perfect reflection. The quantity X is the one way transducer transfer function, i.e. the frequency response of the transducer, with the square exponent indicating the two-way—going and coming—aspect. F is any filtering applied to the received signal within the receiver. D is the one way diffraction or directivity pattern at location u. This phenomena refers to the filtering or spectral alteration of the received signal occurring by the relationship of the transducer configuration and the location of the point scatterer in the radiation field generated by transducer 20.

The factor B identifies the bulk tissue loss for the frequency $\omega$ and the range d. This quantity refers to the well known frequency dependent absorption of ultrasonic signals by the tissue through which the signals pass. The bulk tissue loss for frequency$\omega$ and range d is expressed using the absorption coefficient $\alpha$, (dB/cm MHz) times twice the range d with appropriate factors to construct the bulk loss coefficient which is $$B(\omega,d) = 10^{-\frac{\alpha 2 d \omega}{20 \, 2\pi 10^6}} \qquad (2)$$

The foregoing quantities in the equation deal with the instrumentation and with the effects of tissue other than that of the point scatterer which is being investigated.

The remaining quantities in the equation express properties of the reflected signal. The quantity $Y_o$ represents the magnitude of the reflected signal. The frequency response of the reflected signal is indicated by the quantity S. The time, delay of the reflected signal is expressed by a delay factor in the equation. Thus, the concluding quantities in equation 1 express the magnitude (Y), frequency response (S), and time delay of the backscatter signal.

The extension of equation 1 dealing with a single point scatterer to a large number of scatterers located in same volume, is shown in equation 3.

$$R(\omega) = \quad (3)$$

$$(1/2)V(\omega)X^2(\omega)F(\omega)B(\omega,d)\sum_{i=1}^{M} D_i^2(\omega,u)Y_i S_i(\omega,u)e^{-j\omega Ti}$$

The summation is represented by $\Sigma$ indicating that the summation is occurring between one and some number of scatters M. The quantities appearing before $\Sigma$ are those that do not depend on the number of point scatterers. The quantity following $\Sigma$ are those that are unique to the individual scatterers. This includes reflected signal magnitude $Y_i$, diffraction filtering $D_i$, frequency response $S_i$ and the time delay operator.

Equation 3 indicates that for a tissue medium, such as the myocardium, a signal applied in the form of an ultrasonic pulse will return in the form a continuous power signal indicative of a region of random scattering. This is due to the non-resolvable reflection properties of the tissue forming the myocardium and is in contrast to other ultrasonic imagings i.e., the mitral valve, in which a pulse signal is transmitted and a generally pulse-like signal is received.

Equation 3 may be simplified by the following assumptions. First, the volume undergoing analysis is sufficiently small that the diffraction filtering represented by the quantity D does not change greatly throughout the volume undergoing analysis. This permits the quantity D to be moved to the left of the summation sign. Second, the frequency response $S_i$ can be separated into a frequency component and a spatial component $G_i$. As noted above, the frequency component is known to approximate the power law, so that that quantity can be moved to the left of the summation. This results in equation 4.

$$R(\omega) = \quad (4)$$

$$(1/2)V(\omega)X^2(\omega)F(\omega)B(\omega,d)D^2(\omega,u)S_f(\omega)\sum_{i=1}^{M} G_i(\omega,u)e^{-j\omega Ti}$$

The scattering process $S(\omega,u)$ has been separated into a frequency component and a spatial component indicative of the spectral effects of the spatial ordering of the reflectors as $$S_i(\omega,u) = S_f(\omega)G_i(\omega,u) \quad (5)$$

As noted above, the frequency component is approximately a power law spectrum given by $$S_f(\omega) = R_5 \left[\frac{\omega}{2\pi 5 \cdot 10^6}\right]^P \quad (6)$$

where $R_5$ is an arbitrary constant that is the magnitude of the spectrum at 5 MHz. The spectrum is very nearly a Rayleigh spectrum so that p equals approximately 2.

Using these simplifications for the signals, the ultrasonic equation may be rewritten using an effective transmitted signal as $$R(\omega) = H(\omega) R_5 \sum_{i=1}^{M} G_i(\omega,u)e^{-j\omega Ti} \quad (7)$$

in which H is the effective transmitted signal defined as $$H(\omega) = \quad (8)$$

$$\left(\frac{1}{2}\right)V(\omega)X^2(\omega) F(\omega) B(\omega, d) D^2(\omega, u)\left(\frac{\omega}{2\pi 5 \cdot 10^6}\right)$$

Equation 7 is the simplest expression of the ultrasound equation yet contains all effects of instrumentation, diffraction, bulk tissue loss, and power law spectrum shape for the scattering.

However, because M is such a large number, the attendant complexity must be dealt with in a random manner and approached through statistics.

One approach would be to use the simple value of the received signal R in performing the summation. But since the summation of the received signals in equation 7 is unpredictable it has a statistical prediction of zero and is unsuitable for use.

However, the power or square of the received signal is finite. It is best, and more generally, described by computing its autocorrelation function, or its dual of the power spectrum which is the product of the received signal R at one time $t_1$ and at another time $t_2$.

$$E[r(t_1)r(t_2)] = \int\int d\tau_1 d\tau_2 h(\tau_1 - t_1)h(\tau_2 - t_2) \cdot \quad (9)$$

$$E\left[R_5^2 \sum_i^{M_1} \sum_k^{M_2} g_i\left(\tau_1 c\frac{1}{2}\right)g_k\left(\tau_2 c\frac{1}{2}\right)\right]$$

Equation 10, below, is a statement of the spatial order of the scatters and shows that there is no spatial order to the scatters and hence no spectral shaping caused by the spectral ordering of the scatters.

$$E\left[R_5^2 \sum_i^{M} \sum_k^{M} g_i(u_i) g_i(u_2)\right] = R_5^2 \delta(u_i - u_2) \quad (10)$$

The delta function $\delta()$ indicates the absence of spatial structure in the scatters. The function is also sometimes called the unit pulse or Dirac function. Equation 10 simplifies equation 9 by showing that no consideration need be given to the spatial ordering of the scatterers. Equation 10 also introduces the physical interpretation of $R_5^2$ as product of the reflectivity and density of the scatters and is determined by experimentation.

Inserting equation 10 in equation 9 yields equation 11.

$$R(\tau) = R_h(\tau)R_5^2 <=> |R(\omega)|^2 = |H(\omega)|^2 R_5^2 \quad (11)$$

Equation 11 states that the autocorrelation function of the received signal is equal to the autocorrelation function of the effective transmitted signal times a scale factor $R_5^2$. Stated in spectral terms in the transform indicated by the double headed arrow in equation 11, the power spectrum received is equal to the energy spectrum transmitted scaled by the factor $R_5^2$. In effect, the transmitted pulse signal created a continuous power signal within the scattering region with an identical power spectrum.

By evaluating the autocorrelation function at $\tau = 0$ in equation 11 we can equate the received power to the product of the energy of the transmitted pulse and the scale factor $R_5^2$. Since the energy of the transmitted pulse can be established and the power of the received signal determined, the quantity $R_5$ can be measured and used as an indication of backscatter magnitude.

The expression of equation 11 is in terms of energy per second due to the fact that it is a power expression. Because a second is a long time with respect to the dimensions of the region producing the received signal due to the speed of sound in tissue (1 sec=150,000 cm) it is not a usable dimension. A more reasonable scale factor is the energy per centimeter of tissue which is obtained by scaling by one half the wave speed c (the one half being due to the two way travel of the wave in the tissue). The factor $R_5^2$ is then $$R_5^2 \frac{2}{c}.$$

This quantity becomes the integrated backscatter quantity to be measured. It is conveniently termed Integrated Backscatter Rayleigh at 5 MHz or IBR5 and may be considered to be the energy/cm along the ultrasonic beam. IBR5 is determined from equation 11 by dividing the power of the received signal by the energy of the effective transmitted signal $H(\omega)$. More particularly the magnitude of the integrated backscatter can be determined by rearranging equation 11 with $\tau=0$ to solve for the magnitude of the backscatter. This is done by measuring the power of the received signal and scaling by the energy of the effective transmitted signal represented by the autocorrelation function $R_h(\tau)$ evaluated at $\tau$ equal to zero.

$$IBR5 = \frac{2}{c} \frac{1}{R_h(0)} \left[ \frac{1}{T_a} \int_{t_1-\frac{1}{2}T_a}^{t_1+\frac{1}{2}T_a} r^2(t)dt \right] \quad (13)$$

The quantity in brackets is the power of the received signal at a point in time centered on $t_1$.

It should be noted that Equation 13 is a general equation that will provide a value for IBR5 for many arbitrary choices of effective transmitted wave form $H(\omega)$. The optimal effective transmitted signal is a white, band limited one. This is achieved by selecting $F(\omega)$ as the whitening filter of bandwidth 2W. The factor of the bandwidth 2W of the optimal, white band limited signal band pass filter can be used as the energy of the effective transmitted signal $R_h(0)$ when scaling in accordance with Parseval's theorem.

From the statistical point of view, the quality of the estimate determined above depends on the number of degrees of freedom that are being summed by the integrator as in $$\text{Var }(IBR5) = \frac{IBR5}{2\,W\,T_a} \quad (14)$$

The variance of IBR5 depends on the number of degrees of freedom in the signal. As noted from equation 14 the degrees of freedom are controlled by the product of the bandwidth 2W of the whitened signal and the averaging time $T_a$. An appreciation of this fact can be used in designing the bandwidth of the input filter 110 and the averaging time over which integration occurs in magnitude detector 114. That is, by increasing the bandwidth and reducing the averaging time $T_a$, the variance can be reduced.

Turning now to the details of apparatus 100, FIG. 9 shows a preferred arrangement for carrying out the present invention. The ultrasonic signal generator 24 may comprise a Thévenin voltage source that generates voltage v(t). As shown in FIG. 9 the series resistor 25 in the Thévenin voltage source may typically be 50 ohms. The output of the voltage source is provided through controlled impedance cable 27 having an impedance equal to that of the voltage source, for example, 50 ohms. The other end of the cable is connected to transducer 20.

The input to apparatus 100 is connected intermediate resistor 25 and controlled impedance cable 27, as shown in FIG. 9.

The received signal may be applied to preamplifier 130 that amplifies the magnitude of the received backscatter signal. Amplifier 130 has an infinite input impedance that insures that amplifier 130 will not effect the operation of the ultrasonic signal generator.

The signal amplified from amplifier 130 is passed through band pass filter 132 to remove noise and to establish the processing bandwidth 2W. The output of band pass filter 132 is a signal having a band width 2W between frequencies $f_1$ and $f_2$, as shown ideally in FIG. 9 and unity transmission, also as shown in FIG. 9. The band pass filter may comprise resistive, inductive, and capacitive elements that approach the ideal. Filter 132 may have a bandwidth of, for example 2 MHz that includes the nominal frequency $f_o$ of the transmitted signal and other useful frequencies, while removing noise.

The output of band pass filter 132 may be applied to analog/digital converter 134 it being understood that such conversion is not essential to the practice of the present invention.

The output signal from input circuit 110 is applied to whitening filter 112, shown in FIG. 10, that whitens the spectrum of the received signal with respect to the various factors that alter the spectral content of the received signal R. Whitening filter 112 includes circuitry 150 that removes the influences of the instrumentation on the received ultrasonic backscatter signal so as to "whiten" the signal with respect to instrumentation effects. Such instrumentation influences include those arising from the spectral content of the transmitted ultrasonic pulse signal V, the transducer transfer function or frequency response X, and the diffraction, D.

With respect to whitening received signal R for the spectral content of the transmitted ultrasonic pulse signal V, the spectral content of the transmitted signal is assertained by appropriate signal analysis instruments. A highly simplified showing of the frequency spectrum of the transmitted signal V is shown in FIG. 11A. As noted above, a pulse type signal of a nominal frequency $f_o$ will actually comprise a spectrum of frequencies, both lower and higher than the nominal frequency, as shown in FIG. 11A. The bandwidth $f_1$-$f_2$ established by bandpass filter 132 is also shown in FIG. 11A. The spectral content of the transmitted signal is indicated by the graph $V_{(f)}$.

In order to whiten the spectral content of the transmitted signal V, it is necessary to apply a filtering function to the received signal that is the inverse of the transmitted signal characteristic shown in FIG. 11A. This inverse filtering function is shown in FIG. 11B. The inverse characteristic is identified as $1/V_f$ in FIGS.

11B and 10 at filter 152. The result is the whitened $V_{(f)}$ signal shown in FIG. 11C which is uniform over the $f_1-f_2$ spectrum of the signal $V_{(f)}$. The filtering may be carried out with well known digital signal compensation techniques. If an analog filter is employed, the R, L, C components of filter would be selected to provide the frequency response to the filter shown in FIG. 11B.

The procedure followed with respect to the filtering required due to the transfer function X of transducer 20 and provided by circuit 154 may be similar to that for transmitted signal V. That is, the transducer transfer function may be determined by appropriate calibration procedures. For example, the transducer transfer function may be determined using a self-reciprocity technique in which ultrasonic signals are applied to a planar target of known reflection coefficient and suitable correction. In a manner similar to that shown in FIGS. 11A-C, the spectral alteration produced by transducer transfer function X over the bandwidth of received signal R is determined, the inverse constructed as a filter, and applied to the received signal R to whiten the received signal R for the influences of transducer transfer function X.

It will be appreciated that compensation must be provided for the influences of transducer transfer function upon signal transmission, as well as the influences of transducer transfer function upon signal reception. The factor X is usually considered and defined as the on-way transfer function. It is, therefore, necessary to apply this compensation twice, as indicated by the squared notation in circuit 154.

Compensation for diffraction D is provided by filter 158. Similar to transducer frequency response X, the diffraction influences the ultrasonic signal both during transmission and reception and is thus shown squared in FIG. 10. As noted, supra, diffraction is the alteration in the spectral content of the received signal R due to the positional relationship between transducer 20 and each ultrasonic reflector generating a backscatter signal. Thus, while the compensation provided for transducer frequency response X, and transmitted ultrasonic signal V remain generally constant among all the data points in an ultrasonic scan, the compensation provided for diffraction D differs for each data point.

Diffraction properties may be determined through appropriate calibration procedures by ascertaining the radiation pattern of transducer 20 and by using reflectors of known properties, such as polystyrene microspheres, and a media, such as water, also of known properties to determine the frequency response. Using such data, filter 158 is so formed as to provide the appropriate whitening for diffraction to the signal received from each data point in a scan, i.e. for each distance d along each axis $A_1$ through $A_n$.

In addition to the spectral whitening provided by circuit 150 to compensate for the influences of instrumentation, it is necessary to compensate for the influences of bulk tissue loss B. This loss is evidenced by the attenuation and spectral alteration of the received signal due to the tissue through which the ultrasonic signals pass.

The general formula for determining bulk tissue loss, and hence the corresponding necessary spectral whitening, is given, supra, as equation 2. Determining the actual whitening to be applied for bulk tissue loss involves the extension of the formula to each data point employed in an ultrasonic scan. As can be readily seen from FIG. 1, the amount and type of tissue encountered by the ultrasonic signal from each data point in the scan will be different. For example, the received signal from the right myocardium will pass through no blood, whereas the received signal from the left myocardium will pass through blood as much as four times. The absorption coefficient $\alpha$ for blood employed in equation 2 differs from that of myocardial muscle. The bulk tissue loss for a reflected signal from the left myocardium would be the sum of the losses, as determined by the length along the axis of transmission for each type of tissue and $\alpha$ for each type of tissue, for all the tissue through which the ultrasonic signal must pass. In the case of the left myocardium, this would include the muscle of the right myocardium, the blood of the right ventricle, the tissue of the septum, the blood of the left ventricle, etc.

The amount of whitening to be provided for bulk tissue loss B to each data point in an ultrasonic scan may be determined in a number of ways. For example, if the anatomy of the organ being scanned was known, the bulk tissue loss B whitening for each data point is determined based on that knowledge and applied to the stored ultrasonic signal data for each data point in the scan.

Or, the received backscatter signal data, for example that stored at 508 in FIG. 7A, can be analyzed to determine the tissue region characteristics of the actual anatomy being scanned. The prominent features of the received and stored signals such as those shown in FIGS. 2A and 2B may be used for this purpose. Thereafter, the appropriate absorption coefficients are applied to the various tissue regions and the bulk tissue loss B determined for each data point. From that, the appropriate spectral whitening for bulk tissue loss can be applied to the signal from each data point.

As noted, supra, bulk tissue loss B involves both attenuation and spectral alteration of the received signal. These two factors have been combined in the foregoing discussion. If desired, compensation for these factors can be accomplished separately. The compensation for attenuation would basically comprise range gain compensation that increases the magnitude of the received signals originating at data points deeper into the chest. This range gain compensation could be included in input circuit 110, if desired. Circuitry 160 would then carry out the remaining compensation needed to whiten the received signal R with respect to bulk tissue loss.

As noted in detail, above, the myocardium, itself, has frequency response characteristics for which compensation must be provided. The frequency response characteristic is in the nature of a power law spectrum. FIG. 12A shows the experimentally determined frequency response characteristic of the myocardium. FIG. 12A shows log-frequency response in dB plotted against log frequency for myocardial tissue. In accordance with the power law, backscatter frequency response, statistically resolved through least square linear regression, is a straight line. FIG. 12 shows backscatter data for two different tissue loss values. A pure Rayleigh spectrum would have a slope of 4 (p=2). Experimental evidence indicates the slope of the backscatter graph to lie between 3.1 and 4.1. This permits the Rayleigh slope to be used in a first order model if the actual slope is not known.

FIG. 12A also shows the quantity $R_5$. It is the point on the ordinate corresponding to 5 megahertz on the abscissa.

In the same manner as FIG. 11B, FIG. 12B shows the spectral compensation must be applied by filter 162 to whiten the signal with respect to one of the frequency responses of the myocardium shown in FIG. 12A. In the case of the present example, the gain of filter 162 is set to unity at 5 MHz. FIG. 12C shows the received signal R whitened for myocardial tissue frequency response.

It will be appreciated that, if desired, the spectral content of transmitted signal V may be selected by appropriate construction of generator 24 to simplify or eliminate the whitening required by filter 112. That is, the spectral content of transmitted signal V can be selected so that the frequency response of the body tissue provides the necessary whitening. The wave form of the transmitted signal may also be selected with a view toward simplifying the transmission and reception of the ultrasonic signal. Also, since the bulk tissue loss B is much greater at higher frequencies, the transmitted signal V can have enhanced high frequencies to reduce the amount of bulk tissue loss filtering required. The frequency content of the transmitted signal can also be selected so as to mitigate the effects of noise and/or maintain the dynamic range of the received signal R. Or, some combination of the foregoing may be employed.

It will be appreciated that filters 112 and 110 comprise filter $F(\omega)$ which is a factor in the effective transmitted signal defined in equation 8. By selecting filter $F(\omega)$ as a band limited inverse filter, the whitening process described above is accomplished.

It will also be appreciated that the sequence of filters 110 and 112 can occur in any ordering. If desired, the band limiting and whitening functions may be combined to any desired degree.

The output signal of whitening filter 112 is a whitened signal having spectral intensity $R_S^2$ and a bandwidth of 2W. It is applied to magnitude detector 114 shown in FIG. 13 that determines the maximum likelihood estimate of the magnitude of the intensity of the random ultrasonic backscatter IBR5. The basic operation of magnitude detector 114 is squaring the spectrally whitened signal from filter 112, integrating same, and scaling same so that the output of the magnitude detector is the backscatter magnitude quantity IBR5 in accordance with equation 13.

For this purpose, magnitude detector, 114 contains squaring circuit 170 that squares the spectrally whitened received signal R. It will be appreciated that the squaring of the received signal can be easily carried out on a digital or analog basis. Thereafter, the squared signal from squaring circuit 170 is applied to gate circuit 172 that determines the interval over which the integration will take place. For example, gate 172 may establish an interval of $t_1 \pm \frac{1}{2}T_a$ for performing the integration.

Integrator 174 performs the integration over the interval established by the gate. In accordance with equation 13, it is necessary to divide the output of integrator 174 by the time interval $T_a$ over which the integration took place. This is accomplished by divider 176. The output of divider 176 provides the power of the output of whitening filter 112 to which the appropriate scaling factors can be provided so as to produce backscatter signal magnitude IBR5.

Scalar circuit 180 provides the scaling factors. This includes the quantity 2/c that establishes the backscatter magnitude measurement in energy per centimeter of tissue.

Also, in accordance with equation 13, it must include a factor indicative of the energy of the transmitted signal, represented in that equation by the quantity $1/R_h(0)$ that is the autocorrelation function $R_h(\tau)$ evaluated at $\tau=0$. As noted above, the factor $\frac{1}{2}W$ is the energy of the effective transmitted signal analogous to $R_h(0)$ and is so shown in FIG. 13 as an input to scalar circuit 180.

The application of these scaling factors provide the output signal of magnitude detector 114 as the absolute magnitude of the ultrasonic backscatter IBR5. As noted supra, this magnitude may be used directly by a physician to obtain medically significant data from the ultrasonic backscatter. Or, the intensity magnitude signal may be applied to time averaging circuit 116 to obtain the value of IBR5 averaged over the cardiac cycle. Similarly, the output of magnitude detector 112 may be applied to discrete Fourier transform circuit 118 to obtain the maximum likelihood estimates of the amplitude modulation and phase of the backscatter magnitude. The Fourier transform may be carried out through digital or analog correlation by sine and cosine.

Various modes of carrying out the invention are contemplated as being within the scope of the following claims particularly pointing out and distinctly claiming the subject matter which is regarded as the invention.

I claim:

1. Apparatus for obtaining an optimal measurement of the absolute magnitude of the ultrasonic backscatter from a selected tissue region in a body of tissue, the tissue of the region forming distributed, unresolved ultrasonic reflectors, said apparatus being couplable to means for applying a transmitted ultrasonic signal to the body exteriorly thereof and for receiving a signal having spectral components of frequency at the exterior of the body, said received signal including the backscatter signal from the tissue region, said apparatus comprising:
   means for signal processing the backscatter signal form the region for compensating the backscatter signal for the frequency spectrum alterations contained in the backscatter signal resulting from the frequency response characteristics of the apparatus and the signal transmitting/receiving means, the bulk tissue loss, and the tissue of the region to provide an output in which each spectral component is equally weighted; and
   means coupled to said signal processing means for determining the power of the signal processing means output and providing an output of said power determining means being indicative of the absolute magnitude of the ultrasonic backscatter from the tissue of the region.

2. The apparatus according to claim 1 including bandpass means for limiting the frequency bandwidth of the signal processing means to a band of the received signal containing energy significant, relative to noise, for power determining purposes.

3. The apparatus according to claim 1 including scaling means for providing scaling to the output of said power determining means to provide the magnitude of the ultrasonic backscatter.

4. The apparatus according to claim 3 wherein said scaling means scales by a factor quantifying the indication of the magnitude of the backscatter in a desired manner.

5. The apparatus according to claim 1 including scaling means for providing scaling to the output of the power determining means by a factor quantifying the indication of the magnitude of the backscatter in a desired manner.

6. The apparatus according to claim 1 wherein the signal processing means is further defined as spectrally whitening the received signal to provide said compensation.

7. The apparatus according to claim 6 wherein the signal processing means is further defined as spectrally whitening the received signal for shape and scaling for spectral magnitude to provide said compensation.

8. The apparatus according to claim 6 wherein the frequency response characteristics of the tissue of the region are expressed by a power law and wherein said signal processing means spectrally whitens the received signal to compensate for such power law frequency response characteristics.

9. The apparatus according to claim 8 wherein the frequency response characteristics of the tissue of the region are expressed by a power law in which the intensity of the energy of the backscatter signal is proportional to the ultrasonic signal frequency raised by a power substantially equal to four and wherein said signal processing means spectrally whitens the received signal to compensate for such power law frequency response characteristics.

10. The apparatus according to claim 8 wherein the frequency response characteristics of the tissue of the region are expressed by a power law in which the magnitude of the energy of the backscatter signal is proportional to the ultrasonic signal frequency raised by a power substantially equal to two and wherein said signal processing means spectrally whitens the received signal to compensate for such power law frequency response characteristics.

11. The apparatus according to claim 6 wherein said signal processing means whitens the spectrum of the received signal for the frequency response effects of diffraction.

12. The apparatus according to claim 6 wherein said signal processing means whitens the spectrum of the received signal for the frequency response effects of transducer transfer function.

13. The apparatus according to claim 6 wherein said signal processing means whitens the spectrum of the received signal for the frequency response effects of the transmitted signal characteristics appearing in the received signal.

14. The apparatus according to claim 13 wherein said apparatus includes means for generating the transmitted signal and wherein said generating means generates a transmitted signal having frequency characteristics producing desired frequency effects in the received signal.

15. The apparatus according to claim 1 wherein the bulk tissue loss of the body attenuates the received signal and wherein said apparatus included range gain compensation means for overcoming the effects of the attenuation of the received signal.

16. The apparatus according to claim 1 wherein said power determining means includes means for squaring the output of said signal processing means.

17. The apparatus according to claim 16 wherein said output of said signal processing means includes outputs corresponding to a plurality of data points in said tissue region and said power determining means includes means coupled to said squaring means for providing an average of the squared outputs from data points of a contiguous portion of the tissue of the region.

18. The apparatus according to claim 17 wherein said average providing means includes means for summing the squared outputs form the contiguous tissue portion data points and for dividing the sum by the number of data points in the average.

19. The apparatus according to claim 1 further defined as obtaining the backscatter measurement from th tissue of an organ functioning in a cyclical manner, said apparatus including means for averaging measurements obtained over a plurality of functional cycles of the organ.

20. The apparatus according to claim 1 further defined as obtaining the backscatter measurement from the tissue of an organ functioning in a cyclical manner, said apparatus including means for averaging measurements obtained over the functional cycle of the organ.

21. The apparatus according to claim 1 further defined as obtaining the backscatter measurement from the tissue of an organ functioning in a cyclical manner, the magnitude of the backscatter varying during the functional cycle, said apparatus including means for determining the amplitude modulation characteristics of the varying backscatter signal.

22. The apparatus according to claim 1 further defined as obtaining the backscatter measurement from the tissue of an organ functioning in a cyclical manner, the magnitude of the backscatter signal cyclically varying during the functional cycle of the organ, said apparatus including means for determining the phase of the varying backscatter with respect to the functional cycle of the organ.

23. Apparatus for ultrasonically determining the physiological condition of myocardial tissue, said apparatus being couplable to means for applying a transmitted ultrasonic signal to the exterior of the thorax and for receiving a signal having spectral components of frequency at the exterior of the thorax, said received signal including the backscatter signal form the myocardial tissue, said apparatus comprising:

signal processing means for spectrally whitening the backscatter signal from the myocardial tissue for compensating the backscatter signal for the frequency spectrum alterations contained in the backscatter signal resulting from the frequency response characteristics of the apparatus and the signal transmitting/receiving means, the bulk tissue loss, and the tissue of the myocardium to provide an output in which each spectral component is equally weighted, said output of said signal processing means including outputs corresponding to a plurality of data points in th myocardial tissue;

bandpass means for limiting the frequency bandwidth of the signal processing means to a band containing energy significant, relative to noise, for power determining purposes;

means for determining the power of the signal processing means output, said power determining means including means for squaring the output of said signal processing means, and means for providing an average of the squared data point outputs from a contiguous portion of the myocardial tissue as the output of said power determining means;

scaling means for providing scaling to the output of the power determining means to provide an indication of the absolute magnitude of the ultrasonic backscatter from the myocardial tissue; and means for providing data indicative of the physiological condition of the myocardial tissue from the myocardial tissue ultrasonic backscatter magnitude.

24. The apparatus according to claim 23 wherein said scaling means scales the output of the power determining mean by a factor quantifying the backscatter magnitude in a desired manner.

25. The apparatus according to claim 23 wherein the signal processing means is further defined as spectrally whitening the received signal for shape and scaling for spectral magnitude to provide said compensation.

26. The apparatus according to claim 23 wherein the frequency response characteristics of the myocardial tissue are expressed by a power law in which the intensity of the energy of the backscatter signal is proportional to the ultrasonic signal frequency raised by a power substantially equal to four and wherein said signal processing means spectrally whitens the received signal to compensate for such power law frequency response characteristics.

27. The apparatus according to claim 23 wherein said data providing means averages backscatter magnitudes obtained over a plurality of heart beats.

28. The apparatus according to claim 23 wherein said data providing means averages backscatter magnitudes obtained over a beat of the heart.

29. The apparatus according to claim 23 wherein said data providing means is further defined as determining the amplitude modulation characteristics of the backscatter magnitude.

30. The apparatus according to claim 23 wherein said data providing means is further defined as determining the phase of the backscatter signal magnitude with respect to the heart beat.

31. A method for obtaining an optimal measurement of the absolute magnitude of the ultrasonic backscatter from a selected tissue region in a body of tissue, the tissue of the region forming distributed, unresolved ultrasonic reflectors, a transmitted ultrasonic signal being applied to the body exteriorly thereof and a signal having spectral components of frequency being received at the exterior of the body by instrumentation means, said received signal including the backscatter signal from the tissue region, said method comprising the steps of:
  signal processing the backscatter signal from the region for compensating the backscatter signal for the frequency spectrum alterations contained in the backscatter signal resulting from the frequency response characteristics of the instrumentation means, the bulk tissue loss, and the frequency response characteristics of the tissue of the region to provide an output in which each spectral component is equally weighted; and
  determining the power of the process backscatter signal output and providing a further output, said further output being indicative of the absolute magnitude of the ultrasonic backscatter from the tissue of the region.

32. The method according to claim 31 including the step of limiting the frequency bandwidth of the signal being processed to a band containing energy significant, relative to noise, for power determining purposes.

33. The method according to claim 31 including the step of scaling to provide the magnitude of the ultrasonic backscatter in the further output.

34. The method according to claim 33 wherein the scaling step is further defined as scaling by a factor quantifying the indication of the magnitude of the backscatter in a desired manner.

35. The method according to claim 31 including the step of scaling by a factor quantifying the indication of the magnitude of the backscatter in a desired manner.

36. The method according to claim 31 wherein the signal processing step is further defined as spectrally whitening the received signal to provide said compensation.

37. The method according to claim 36 wherein the signal processing step is further defined as spectrally whitening the received signal for shape and scaling for spectral magnitude to provide said compensation.

38. The method according to claim 36 wherein the frequency response characteristics of the tissue region are expressed by a power law and wherein said signal processing step spectrally whitens the received signal to compensate for such power law frequency response characteristics.

39. The method according to claim 38 wherein the frequency response characteristics of the tissue of the region are expressed by a power law in which the intensity of the energy of the backscatter signal is proportional to the ultrasonic signal frequency raised by a power substantially equal to four and wherein said signal processing step spectrally whitens the received signal to compensate for such power law frequency response characteristics.

40. The method according to claim 38 wherein the frequency response characteristics of the tissue of the region are expressed by a power law in which the magnitude of the energy of the backscatter signal is proportional to the ultrasonic signal raised by a power substantially equal to two and wherein said signal processing step spectrally whitens the received signal to compensate for such power law frequency response characteristics.

41. The method according to claim 36 wherein said signal processing step whitens the spectrum of the received signal for the frequency response effects of diffraction.

42. The method according to claim 36 wherein said signal processing step whitens the spectrum of the received signal for the frequency response effects of transducer transfer function.

43. The method according to claim 36 wherein said signal processing step whitens the spectrum of the received signal for the frequency response effects of the transmitted signal characteristic appearing in the received signal.

44. The method according to claim 43 including the step of generating the transmitted signal with frequency characteristics producing desired frequency effects in the received signal.

45. The method according to claim 31 wherein the bulk tissue loss of the body attenuates the received signal and wherein the method includes the step of overcoming the effects of the attenuation of the received signal.

46. The method according to claim 31 wherein said power determining step includes the step of squaring the output of the signal processing step.

47. The method according to claim 46 wherein said output of said signal processing step includes outputs corresponding to a plurality of data points in said tissue of the region and said power determining step is further defined as providing an average of the squared outputs from data points of a contiguous portion of the tissue of the region.

48. The method according to claim 47 wherein said average providing step is further defined as summing the squared outputs from the contiguous tissue portion data points and dividing the sum by the number of data points in the average.

49. The method according to claim 31 further defined as obtaining the backscatter measurement from the tissue of an organ functioning in a cyclical manner, said method including the step of averaging measurements obtained over a plurality of functional cycles of the organ.

50. The method according to claim 31 further defined as obtaining the backscatter measurement from the tissue of an organ functioning in a cyclical manner, said method including the step of averaging measurements obtained over the functional cycle of the organ.

51. The method according to claim 31 further defined as obtaining the backscatter measurement from the tissue of an organ functioning in a cyclical manner, the magnitude of the backscatter varying during the functional cycle, said method including the step of determining the amplitude modulation characteristics of the varying backscatter signal.

52. The method according to claim 31 further defined as obtaining the backscatter measurement from the tissue of an organ functioning in a cyclicla manner, the magnitude of the backscatter signal cyclically varying during the functional cycle of the organ, said method including the step of determining the phase of the varying backscatter signal with respect to the functional cycle of the organ.

53. A method for ultrasonically determining the physiological condition of myocardial tissue, a transmitted ultrasonic signal being applied to the thorax exteriorly thereof and signal having spectral components of frequency being received at the exterior of the thorax by instrumentation means, said received signal including the backscatter signal from the myocardial tissue, said method comprising the steps of:

spectrally whitening the backscatter signal from the myocardial tissue for compensating the backscatter signal for the frequency spectrum alterations contained in the backscatter signal resulting from the frequency response characteristics of the instrumentation means, the bulk tissue loss, and tissue of the myocardium to provide an output in which each spectral component is equally weighted, said spectrally whitened backscatter signal output including outputs corresponding to a plurality of data points in the myocardial tissue;

limiting the frequency bandwidth of the signal being spectrally whitened to a band containing energy significant, relative to noise, for power determining purposes;

determining the power of the spectrally whitened backscatter signal output and providing a further output by squaring the spectrally whitened backscatter signal output and averaging the squared data point outputs from a contiguous portion of the tissue of the region as the further output;

scaling to provide an indication of the absolute magnitude of the ultrasonic backscatter from the myocardial tissue; and providing data indicative of the physiological condition of the myocardial tissue from the myocardial tissue ultrasonic backscatter magnitude.

54. The method according to claim 53 including the step of scaling by a factor quantifying the backscatter magnitude in a desired manner.

55. The method according to claim 53 wherein the spectrally whitened step is further defined as spectrally whitening the received signal for shape and scaling for spectral magnitude to provide said compensation.

56. The method according to claim 53 wherein the frequency response characteristics of the myocardial tissue are expressed by a power law in which the intensity of the energy of the backscatter signal is proportional to the ultrasonic signal frequency raised by a power substantially equal to four and wherein said signal spectrally whitening spectrally whitens the received signal to compensate for such power law frequency response characteristics.

57. The method according to claim 53 wherein the data providing step is further defined as averaging measurements obtained over a plurality of heart beats.

58. The method according to claim 53 wherein the data providing step is further defined as averaging measurements obtained over a beat of the heart.

59. The method according to claim 53 wherein the data providing step is further defined as determining the amplitude modulation characteristics of the backscatter magnitude.

60. The method according to claim 53 wherein the data providing step is further defined as determining the phase of the backscatter magnitude with respect to the heart beat.

* * * * *